(12) United States Patent
Chen et al.

(10) Patent No.: US 12,252,487 B2
(45) Date of Patent: Mar. 18, 2025

(54) DOMINANT SALT FORMS OF PYRIMIDINE DERIVATIVES, AND CRYSTAL FORMS THEREOF

(71) Applicant: GUANGDONG RAYNOVENT BIOTECH CO., LTD., Guangzhou (CN)

(72) Inventors: Xiaoxin Chen, Guangzhou (CN); Chengwu Liu, Guangzhou (CN); Zhuowei Liu, Guangzhou (CN); Zhenyou Tan, Guangzhou (CN); Zhiqiang Liu, Guangzhou (CN); Zhiwei Cheng, Guangzhou (CN); Chaofeng Long, Guangzhou (CN); Jiajun Huang, Guangzhou (CN); Guangqiang Zhou, Guangzhou (CN)

(73) Assignee: GUANGDONG RAYNOVENT BIOTECH CO., LTD., Guangzhou (CN)

( * ) Notice: Subject to any disclaimer, the term of this patent is extended or adjusted under 35 U.S.C. 154(b) by 698 days.

(21) Appl. No.: 17/628,496

(22) PCT Filed: Jun. 24, 2020

(86) PCT No.: PCT/CN2020/097967
§ 371 (c)(1),
(2) Date: Jan. 19, 2022

(87) PCT Pub. No.: WO2021/012864
PCT Pub. Date: Jan. 28, 2021

(65) Prior Publication Data
US 2022/0380363 A1    Dec. 1, 2022

(30) Foreign Application Priority Data

Jul. 22, 2019  (CN) .......................... 201910660153.1

(51) Int. Cl.
*C07D 471/04*    (2006.01)
(52) U.S. Cl.
CPC ........ *C07D 471/04* (2013.01); *C07B 2200/13* (2013.01)
(58) Field of Classification Search
None
See application file for complete search history.

(56) References Cited

U.S. PATENT DOCUMENTS 11,535,613 B2 *  12/2022  Xiong ................. C07D 471/04

FOREIGN PATENT DOCUMENTS

| CN | 103492381 A | 1/2014 |
| CN | 104922128 A | 9/2015 |
| CN | 106573920 A | 4/2017 |
| WO | 2017133667 A1 | 8/2017 |
| WO | 2018041263 A1 | 3/2018 |
| WO | 2019170067 A1 | 9/2019 |

\* cited by examiner

*Primary Examiner* — Adam C Milligan
*Assistant Examiner* — Jed A Kucharczk
(74) *Attorney, Agent, or Firm* — D'Ambrosio & Menon, PLLC; Usha Menon

(57) ABSTRACT

Disclosed are sodium salts of pyrimidine derivatives, and a series of crystal forms thereof. The series of crystal forms exhibit a good druggability, such as stability, fluidity, compressibility, etc., and provide a variety of options of APIs for subsequent drug product development.

14 Claims, 30 Drawing Sheets

DOMINANT SALT FORMS OF PYRIMIDINE DERIVATIVES, AND CRYSTAL FORMS THEREOF

CROSS-REFERENCE TO RELATED APPLICATION

The present application is a national phase entry under 35 USC § 371 of International Application PCT/CN2020/097967, filed Jun. 24, 2020, which claims the benefit of and priority to Chinese Patent Application No. 2019106601531, filed Jul. 22, 2019, the entire disclosures of which are incorporated herein by reference.

TECHNICAL FIELD

The present disclosure belongs to the field of pharmaceutical chemistry, especially to a series of dominant salt forms of pyrimidine derivatives and crystal forms thereof, as well as methods for preparing the dominant salt forms and the crystal forms thereof, and active pharmaceutical ingredients (APIs) and pharmaceutical compositions including the dominant salt forms and the crystal forms thereof.

BACKGROUND

Flu virus, i.e., influenza virus (IFV), is a segmented, single-stranded and antisense RNA virus that can cause influenza in humans and animals. Influenza outbreak will cause thousands of deaths, result in great social panic, and increase social instability.

Influenza can give rise to direct costs due to productivity loss and related medical resources, as well as indirect costs due to preventive measures. In the United States, influenza has caused cumulative damage of about $10 billion per year. It is estimated that future influenza pandemics may cause hundreds of billions of dollars in direct and indirect costs. The cost for preventing influenza is also very high. Governments around the world have spent billions of dollars in preparing and planning for possible H5N1 avian influenza pandemics. The cost is associated with the purchase of drugs and vaccines, as well as the development of disaster drills and strategies to improve border control.

Current options of influenza therapy include vaccination, as well as chemotherapy and chemoprevention with antiviral drugs. Antiviral drugs can also be used to treat influenza. Of those, neuraminidase inhibitors, such as, oseltamivir (Tamiflu), have obvious effects on Influenza A virus. However, clinical observation shows that virus strains resistant to these neuraminidase inhibitors have emerged. In the field of anti-influenza virus, there is an urgent clinic need for anti-influenza viral drugs with new action mechanisms, which can support the treatment of Influenza A by monotherapy, or can be used in combination with commercially available anti-influenza viral drugs with other action mechanisms for the prevention and treatment of Influenza A.

The patent application WO2018041263 discloses a series of pyrimidine derivatives. In vitro activity data show that some compounds exhibit positive effects in the experiments of inhibiting the replication of influenza viruses. In further animal experiments, some compounds also exhibit significant therapeutic effects on mouse infection models with Influenza A virus H1N1. Of those, the comprehensive performance of Compound WX-216 (Example 4) is relatively outstanding, which is considered to have good pharmaceutical prospects.

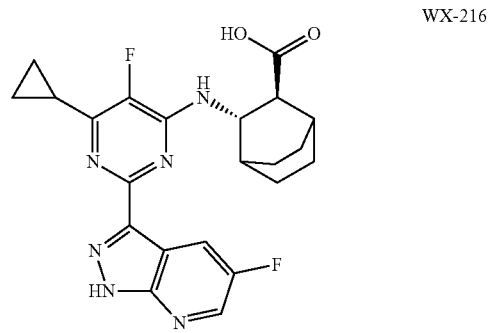 [SMILES: O=C(O)[C@H]1C2CCC(CC2)[C@@H]1Nc1nc(-c2n[nH]c3ncc(F)cc23)nc(C2CC2)c1F]

The patent application WO2019170067 discloses a series of crystal forms, salt forms and crystal forms of salt forms of WX-216. The series of salt forms/crystal forms have good stability and production/clinical application prospect, and provide a variety of options of intermediate products and/or APIs for large-scale production of APIs and downstream process of pharmaceutical products (e.g., pharmaceutical process).

Screening of salt forms and crystal forms is one of the important links in drug development. For specific compounds, the advantages and disadvantages of physical and chemical properties of its free state, various salt forms and corresponding crystal forms are unknown. Based on a further consideration of its druggability, it is of great significance for drug development to find suitable salt forms and corresponding dominant crystal forms thereof to provide a variety of options of intermediate products and/or APIs for subsequent drug development.

SUMMARY

The present disclosure first discloses sodium salts of WX-216 (Compound 1), and first provides a series of crystal forms of Compound 1 which have good druggability (e.g., stability, flowability, compressibility, etc.) and provide a variety of API options for subsequent drug development.

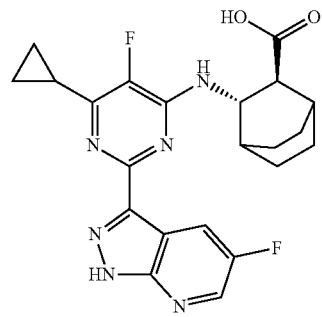

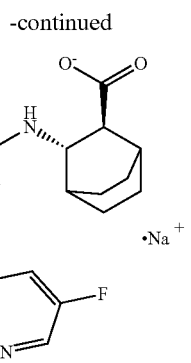

Compound 1

Specially, WX-216 is a carboxyl-containing pyrimidine derivative. Those skilled in the art can appreciate that WX-216 can form sodium salts. Further experimental studies show that Compound 1 is mono-sodium salt of WX-216, namely, one WX-216 molecule is combined with one Na$^+$ ion to form sodium salt in a well-known salt-forming manner in the art. It is a case where an organic compound forms metal sodium salt, which is well known in the art. The present disclosure relates to a series of crystal forms of Compound 1, including but not limited to unsolvated and solvated forms of Compound 1. The term "Solvent" involved in the term "unsolvated and solvated forms" includes water and organic solvents, including but not limited to methanol, ethanol, propanol, isopropanol, acetone, butanone, acetonitrile, dichloromethane, trichloromethane, ethyl acetate and the like commonly seen in the art.

For characterization of crystal forms of Compound 1, those skilled in the art can appreciate that for a specific crystal form of a specific compound, there are fluctuations in 2θ angles of diffraction peaks in the X-ray powder diffraction (XRPD) pattern thereof in repeated experiments due to instrument equipment, operational methods, sample purity, human factors and the like during characterization, and the fluctuation range (error range) is usually within ±0.2°. In addition, those skilled in the art can also appreciate that the stability and repeatability of diffraction peaks will be comprehensively affected by 2θ angle of individual diffraction peak in the XRPD pattern, absorption intensity (peak height) and other factors. Specially, diffraction peaks which have stronger absorption intensity, better separation, and smaller 2θ angle have better stability and repeatability, and are more suitable for characterizing the specific crystal form. Rather, diffraction peaks which have larger 2θ angle and/or poorer separation and/or weaker intensity may fluctuate to a greater extent due to instrument equipment, operational methods, sample purity, human factors and the like, and may not be repeated in the repeated experiments; therefore, for those skilled in the art, such absorption peaks are not necessary diffraction peaks for characterizing the crystal form. More specially, the present disclosure follows the consensus on crystal form characterization in the art, that is, the diffraction peaks are selected by comprehensively considering 2θ angle, absorption intensity (peak height) and other factors, and grouped in accordance with stability and repeatability.

Those skilled in the art can also appreciate that for the differential scanning calorimetric (DSC) curve and the thermogravimetric analysis (TGA) curve of a sample, there are also fluctuations in the detection results of samples from the same and/or different batches due to instruments, detecting conditions, detecting personnel, etc. Therefore, the present disclosure follows the consensus on crystal form characterization in the art, and sets the fluctuation range of starting points of endothermic and exothermic peaks in the DSC pattern as ±3° C., and the fluctuation range of weight loss in the TGA pattern as ±1%.

Unless otherwise indicated, the term "room temperature" in the present disclosure refers to 25±5° C.; and the "no remarkable weight loss" in the thermogravimetric analysis (TGA) curve in the present disclosure means that the weight loss is ≤1% at the temperature of the detection end point.

The first object of the present disclosure is to provide a crystal form I of Compound 1 and a method of preparing the same, wherein the crystal form shows good druggability.

In particular, the XRPD pattern of the above-mentioned crystal form I of Compound 1 has stably occurred diffraction peaks at angles 2θ of 6.4, 9.8, 12.8, 15.8, 16.2, 17.8, 18.7, 19.3, 20.3, 24.0, 24.6, 27.6, 28.1±0.2°.

Further, the XRPD pattern of the above-mentioned crystal form I of Compound 1 further has diffraction peaks at angles 2θ of 9.0, 15.3, 17.4, 23.1, 28.4±0.2°.

Further, in some embodiments of the present disclosure, the diffraction peaks of the XRPD pattern of the above-mentioned crystal form I of Compound 1 is as shown in the table below:

| No. | 2θ (±0.2°) | Peak Height % |
|---|---|---|
| 1 | 6.4 | 100.0 |
| 2 | 9.0 | 7.1 |
| 3 | 9.8 | 18.4 |
| 4 | 12.8 | 13.7 |
| 5 | 14.4 | 4.7 |
| 6 | 15.3 | 6.4 |
| 7 | 15.8 | 35.4 |
| 8 | 16.2 | 13.9 |
| 9 | 17.4 | 6.6 |
| 10 | 17.8 | 11.0 |
| 11 | 18.7 | 16.4 |
| 12 | 19.3 | 21.6 |
| 13 | 20.3 | 13.9 |
| 14 | 21.4 | 4.5 |
| 15 | 22.1 | 2.7 |
| 16 | 23.1 | 7.2 |
| 17 | 23.6 | 3.3 |
| 18 | 24.0 | 13.6 |
| 19 | 24.2 | 11.4 |
| 20 | 24.6 | 11.8 |
| 21 | 26.3 | 3.8 |
| 22 | 26.5 | 4.5 |
| 23 | 27.6 | 10.8 |
| 24 | 28.1 | 10.1 |
| 25 | 28.4 | 7.5 |
| 26 | 28.8 | 3.6 |
| 27 | 29.8 | 2.8 |
| 28 | 35.2 | 2.9 |

Further, in some embodiments of the present disclosure, the XRPD pattern of the above-mentioned crystal form I of Compound 1 is substantially as shown in FIG. 1.

The DSC curve of the above-mentioned crystal form I of Compound 1 has starting points of endothermic peaks at 51.6, 158.2, and 335.9±3° C., and a starting point of an exothermic peak at 230.4±3° C.

Further, in some embodiments of the present disclosure, the DSC pattern of the above-mentioned crystal form I of Compound 1 is substantially as shown in FIG. 2.

The TGA curve of the above-mentioned crystal form I of Compound 1 exhibits a weight loss of 12.06±1% at 200° C. In particular, the TGA curve exhibits a weight loss of 5.85±1% at 100° C., followed by an additional weight loss of 6.21±1% at 200° C.

Further, in some embodiments of the present disclosure, the TGA pattern of the above-mentioned crystal form I of Compound 1 is substantially as shown in FIG. 3.

The second object of the present disclosure is to provide a crystal form II of Compound 1 and a method of preparing the same, wherein the crystal form shows good druggability.

In particular, the XRPD pattern of the above-mentioned crystal form II of Compound 1 has stably occurred diffraction peaks at angles 2θ of 5.8, 9.3, 10.0, 11.6, 13.7, 17.0, 18.9, 22.8, 24.2±0.2°.

Further, the XRPD pattern of the above-mentioned crystal form II of Compound 1 further has diffraction peaks at angles 2θ of 12.4, 17.7, 21.0, 22.2, 30.1±0.2°.

Further, in some embodiments of the present disclosure, the diffraction peaks of the XRPD pattern of the above-mentioned crystal form II of Compound 1 is as shown in the table below:

| No. | 2θ (±0.2°) | Peak Height % |
|---|---|---|
| 1 | 5.8 | 100.0 |
| 2 | 9.3 | 18.7 |
| 3 | 10.0 | 18.8 |
| 4 | 11.6 | 8.3 |
| 5 | 12.4 | 3.0 |
| 6 | 13.7 | 5.2 |
| 7 | 15.3 | 1.9 |
| 8 | 17.0 | 17.8 |
| 9 | 17.7 | 3.4 |
| 10 | 18.9 | 7.9 |
| 11 | 21.0 | 2.8 |
| 12 | 21.2 | 2.4 |
| 13 | 22.2 | 3.7 |
| 14 | 22.8 | 5.7 |
| 15 | 24.2 | 7.2 |
| 16 | 24.9 | 2.8 |
| 17 | 25.4 | 2.3 |
| 18 | 26.5 | 2.0 |
| 19 | 30.1 | 4.0 |

Further, in some embodiments of the present disclosure, the XRPD pattern of the above-mentioned crystal form II of Compound 1 is substantially as shown in FIG. 5.

The DSC curve of the above-mentioned crystal form II of Compound 1 has a starting point of an endothermic peak at 335.9±3° C.

Further, in some embodiments of the present disclosure, the DSC pattern of the above-mentioned crystal form II of Compound 1 is substantially as shown in FIG. 6.

The TGA curve of the above-mentioned crystal form II of Compound 1 does not exhibit a remarkable weight loss before 300° C.

Further, in some embodiments of the present disclosure, the TGA pattern of the above-mentioned crystal form II of Compound 1 is substantially as shown in FIG. 7.

The third object of the present disclosure is to provide a crystal form III of Compound 1 and a method of preparing the same, wherein the crystal form shows good druggability.

In particular, the XRPD pattern of the above-mentioned crystal form III of Compound 1 has stably occurred diffraction peaks at angles 2θ of 4.6, 5.4, 7.1, 9.7, 10.8, 12.4, 15.1, 17.0, 17.8, 18.9, 19.6, 20.7, 21.8, 23.7, 25.0±0.2°.

Further, the XRPD pattern of the above-mentioned crystal form III of Compound 1 further has diffraction peaks at angles 2θ of 13.6, 14.1, 20.1, 21.3, 24.3, 26.1, 26.5, 28.4, 30.0±0.2°.

Further, in some embodiments of the present disclosure, the diffraction peaks of the XRPD pattern of the above-mentioned crystal form III of Compound 1 is as shown in the table below:

| No. | 2θ (±0.2°) | Peak Height % |
|---|---|---|
| 1 | 4.6 | 10.5 |
| 2 | 5.4 | 45.2 |
| 3 | 7.1 | 17.9 |
| 4 | 9.7 | 100.0 |
| 5 | 10.8 | 13.6 |
| 6 | 12.4 | 26.8 |
| 7 | 13.6 | 9.1 |
| 8 | 14.1 | 7.8 |
| 9 | 15.1 | 18.1 |
| 10 | 16.3 | 5.7 |
| 11 | 17.0 | 12.9 |
| 12 | 17.8 | 24.1 |
| 13 | 18.9 | 12.0 |
| 14 | 19.6 | 11.2 |
| 15 | 20.1 | 7.4 |
| 16 | 20.7 | 10.5 |
| 17 | 21.3 | 8.5 |
| 18 | 21.8 | 15.5 |
| 19 | 22.3 | 5.0 |
| 20 | 23.7 | 24.2 |
| 21 | 24.3 | 9.1 |
| 22 | 25.0 | 11.9 |
| 23 | 25.6 | 6.5 |
| 24 | 26.1 | 8.8 |
| 25 | 26.5 | 8.4 |
| 26 | 27.4 | 6.7 |
| 27 | 28.2 | 7.9 |
| 28 | 28.4 | 7.8 |
| 29 | 30.0 | 5.9 |

Further, in some embodiments of the present disclosure, the XRPD pattern of the above-mentioned crystal form III of Compound 1 is substantially as shown in FIG. 9.

The DSC curve of the above-mentioned crystal form III of Compound 1 has starting points of endothermic peaks at 33.5, and 329.0±3° C., and a starting point of an exothermic peak at 272.1±3° C.

Further, in some embodiments of the present disclosure, the DSC pattern of the above-mentioned crystal form III of Compound 1 is substantially as shown in FIG. 10.

The TGA curve of the above-mentioned crystal form III of Compound 1 exhibits a weight loss of 11.40±1% at 200° C.

Further, in some embodiments of the present disclosure, the TGA pattern of the above-mentioned crystal form III of Compound 1 is substantially as shown in FIG. 11.

The fourth object of the present disclosure is to provide a crystal form IV of Compound 1 and a method of preparing the same, wherein the crystal form shows good druggability.

In particular, the XRPD pattern of the above-mentioned crystal form IV of Compound 1 has stably occurred diffraction peaks at angles 2θ of 5.7, 6.9, 9.3, 12.3, 14.3, 16.7, 17.8, 18.7, 19.3, 20.6, 23.8, 28.4±0.2°.

Further, the XRPD pattern of the above-mentioned crystal form IV of Compound 1 further has diffraction peaks at angles 2θ of 18.2, 18.9, 19.5, 21.6, 27.2, 30.5±0.2°.

Further, in some embodiments of the present disclosure, the diffraction peaks of the XRPD pattern of the above-mentioned crystal form TV of Compound 1 is as shown in the table below:

| No. | 2θ (±0.2°) | Peak Height % |
|---|---|---|
| 1 | 5.7 | 9.4 |
| 2 | 6.9 | 100.0 |
| 3 | 9.3 | 41.8 |
| 4 | 9.9 | 1.9 |
| 5 | 12.3 | 14.1 |
| 6 | 13.9 | 7.6 |
| 7 | 14.3 | 39.4 |
| 8 | 15.5 | 14.4 |
| 9 | 16.2 | 5.3 |
| 10 | 16.7 | 10.8 |
| 11 | 17.8 | 14.2 |
| 12 | 18.2 | 14.4 |
| 13 | 18.7 | 12.6 |
| 14 | 18.9 | 5.4 |
| 15 | 19.3 | 26.3 |
| 16 | 19.5 | 11.9 |
| 17 | 20.6 | 28.7 |
| 18 | 20.9 | 5.4 |
| 19 | 21.6 | 12.8 |
| 20 | 22.4 | 5.2 |
| 21 | 23.5 | 8.9 |
| 22 | 23.8 | 42.7 |
| 23 | 24.2 | 7.2 |
| 24 | 25.0 | 2.6 |
| 25 | 25.9 | 7.8 |
| 26 | 27.2 | 7.6 |
| 27 | 27.7 | 3.3 |
| 28 | 28.4 | 18.8 |
| 29 | 29.4 | 4.7 |
| 30 | 30.5 | 5.4 |

Further, in some embodiments of the present disclosure, the XRPD pattern of the above-mentioned crystal form IV of Compound 1 is substantially as shown in FIG. 13.

The DSC curve of the above-mentioned crystal form IV of Compound 1 has a starting point of an endothermic peak at 326.3±3° C.

Further, in some embodiments of the present disclosure, the DSC pattern of the above-mentioned crystal form IV of Compound 1 is substantially as shown in FIG. 14.

The TGA curve of the above-mentioned crystal form IV of Compound 1 does not exhibit a remarkable weight loss before 300° C.

Further, in some embodiments of the present disclosure, the TGA pattern of the above-mentioned crystal form IV of Compound 1 is substantially as shown in FIG. 15.

The fifth object of the present disclosure is to provide a crystal form V of Compound 1 and a method of preparing the same, wherein the crystal form shows good druggability.

In particular, the XRPD pattern of the above-mentioned crystal form V of Compound 1 has stably occurred diffraction peaks at angles 2θ of 7.1, 9.4, 12.3, 15.5, 18.8, 19.8, 20.9, 25.5, 27.1±0.2°.

Further, the XRPD pattern of the above-mentioned crystal form V of Compound 1 further has diffraction peaks at angles 2θ of 12.8, 16.0, 16.3, 16.5, 20.0, 21.4, 22.2, 22.5, 23.3, 24.7, 25.7, 26.5, 31.2±0.2°.

Further, in some embodiments of the present disclosure, the diffraction peaks of the XRPD pattern of the above-mentioned crystal form V of Compound 1 is as shown in the table below:

| No. | 2θ (±0.2°) | Peak Height % |
|---|---|---|
| 1 | 7.1 | 73.4 |
| 2 | 9.4 | 100.0 |
| 3 | 12.3 | 43.6 |
| 4 | 12.8 | 5.5 |
| 5 | 14.2 | 3.1 |
| 6 | 15.5 | 48.2 |
| 7 | 16.0 | 7.4 |
| 8 | 16.3 | 9.5 |
| 9 | 16.5 | 12.2 |
| 10 | 16.8 | 4.2 |
| 11 | 17.9 | 6.4 |
| 12 | 18.8 | 26.6 |
| 13 | 19.8 | 19.4 |
| 14 | 20.0 | 6.1 |
| 15 | 20.9 | 11.8 |
| 16 | 21.4 | 8.1 |
| 17 | 22.2 | 9.5 |
| 18 | 22.5 | 8.9 |
| 19 | 23.3 | 5.2 |
| 20 | 24.7 | 10.5 |
| 21 | 25.0 | 4.3 |
| 22 | 25.5 | 10.2 |
| 23 | 25.7 | 8.8 |
| 24 | 26.5 | 6.2 |
| 25 | 27.1 | 14.2 |
| 26 | 28.3 | 6.3 |
| 27 | 30.5 | 4.2 |
| 28 | 31.2 | 7.2 |
| 29 | 32.9 | 6.3 |

Further, in some embodiments of the present disclosure, the XRPD pattern of the above-mentioned crystal form V of Compound 1 is substantially as shown in FIG. 16.

The DSC curve of the above-mentioned crystal form V of Compound 1 has a starting point of an endothermic peak at 339.1±3° C.

Further, in some embodiments of the present disclosure, the DSC pattern of the above-mentioned crystal form V of Compound 1 is substantially as shown in FIG. 17.

The TGA curve of the above-mentioned crystal form V of Compound 1 exhibits a weight loss of 1.26±1% before 75° C.

Further, in some embodiments of the present disclosure, the TGA pattern of the above-mentioned crystal form V of Compound 1 is substantially as shown in FIG. 18.

The sixth object of the present disclosure is to provide a crystal form VI of Compound 1 and a method of preparing the same.

In particular, the XRPD pattern of the above-mentioned crystal form VI of Compound 1 has stably occurred diffraction peaks at angles 2θ of 6.9, 9.2, 12.0, 15.2, 16.0, 18.5, 19.5, 25.4, 26.6, 28.2, 32.4±0.2°.

Further, the XRPD pattern of the above-mentioned crystal form VI of Compound 1 further has diffraction peaks at angles 2θ of 21.0, 21.9, 24.6, 27.1±0.2°.

Further, in some embodiments of the present disclosure, the diffraction peaks of the XRPD pattern of the above-mentioned crystal form VI of Compound 1 is as shown in the table below:

| No. | 2θ (±0.2°) | Peak Height % |
|---|---|---|
| 1 | 6.9 | 61.4 |
| 2 | 9.2 | 100.0 |
| 3 | 12.0 | 45.4 |
| 4 | 12.6 | 4.2 |
| 5 | 15.2 | 33.7 |
| 6 | 16.0 | 13.9 |
| 7 | 16.6 | 2.7 |
| 8 | 18.5 | 27.4 |
| 9 | 19.5 | 18.1 |
| 10 | 19.8 | 4.2 |
| 11 | 21.0 | 5.8 |
| 12 | 21.9 | 4.8 |
| 13 | 22.3 | 3.0 |
| 14 | 24.0 | 2.6 |
| 15 | 24.6 | 7.8 |
| 16 | 25.1 | 6.1 |
| 17 | 25.4 | 17.4 |
| 18 | 26.6 | 11.0 |
| 19 | 27.1 | 4.5 |
| 20 | 28.2 | 10.5 |
| 21 | 28.5 | 2.9 |
| 22 | 30.7 | 4.1 |
| 23 | 32.4 | 8.4 |

Further, in some embodiments of the present disclosure, the XRPD pattern of the above-mentioned crystal form VI of Compound 1 is substantially as shown in FIG. 20.

The DSC curve of the above-mentioned crystal form VI of Compound 1 has starting points of endothermic peaks at 25.6, and 330.9±3° C.

Further, in some embodiments of the present disclosure, the DSC pattern of the above-mentioned crystal form VI of Compound 1 is substantially as shown in FIG. 21.

The TGA curve of the above-mentioned crystal form VI of Compound 1 exhibits a weight loss of 3.45±1% at 200° C.

Further, in some embodiments of the present disclosure, the TGA pattern of the above-mentioned crystal form VI of Compound 1 is substantially as shown in FIG. 22.

The seventh object of the present disclosure is to provide a crystal form VII of Compound 1 and a method of preparing the same, wherein the crystal form shows good druggability.

In particular, the XRPD pattern of the above-mentioned crystal form VII of Compound 1 has stably occurred diffraction peaks at angles 2θ of 4.6, 5.8, 7.3, 7.8, 11.3, 14.6, 18.4±0.2°.

Further, in some embodiments of the present disclosure, the diffraction peaks of the XRPD pattern of the above-mentioned crystal form VII of Compound 1 is as shown in the table below:

| No. | 2θ (±0.2°) | Peak Height % |
|---|---|---|
| 1 | 4.6 | 4.7 |
| 2 | 5.8 | 6.7 |
| 3 | 7.3 | 100.0 |
| 4 | 7.8 | 5.0 |
| 5 | 11.3 | 8.4 |
| 6 | 14.6 | 13.2 |
| 7 | 18.4 | 11.3 |

Further, in some solutions of the present disclosure, the XRPD pattern of the above-mentioned crystal form VII of Compound 1 is substantially as shown in FIG. 23.

The DSC curve of the above-mentioned crystal form VII of Compound 1 has starting points of endothermic peaks at 71.8±3° C., and 327.4±3° C., and a starting point of an exothermic peak at 252.0±3° C.

Further, in some embodiments of the present disclosure, the DSC pattern of the above-mentioned crystal form VII of Compound 1 is substantially as shown in FIG. 24.

The TGA curve of the above-mentioned crystal form VII of Compound 1 exhibits a weight loss of 9.18±1% at 200° C.

Further, in some embodiments of the present disclosure, the TGA pattern of the above-mentioned crystal form VII of Compound 1 is substantially as shown in FIG. 25.

The eighth object of the present disclosure is to provide a crystal form VIII of Compound 1 and a method of preparing the same, wherein the crystal form shows good druggability.

In particular, the XRPD pattern of the above-mentioned crystal form VIII of Compound 1 has stably occurred diffraction peaks at angles 2θ of 6.0, 7.0, 7.6, 11.0, 12.2, 14.1, 14.4, 15.4, 18.7, 20.0, 27.8±0.2°.

Further, the XRPD pattern of the above-mentioned crystal form VIII of Compound 1 further has diffraction peaks at angles 2θ of 4.6, 9.3, 15.7, 21.8, 22.2, 25.0, 28.5±0.2°.

Further, in some embodiments of the present disclosure, the diffraction peaks of the XRPD pattern of the above-mentioned crystal form VIII of Compound 1 is as shown in the table below:

| No. | 2θ (±0.2°) | Peak Height % |
|---|---|---|
| 1 | 4.6 | 3.4 |
| 2 | 6.0 | 29.3 |
| 3 | 7.0 | 100.0 |
| 4 | 7.6 | 35.3 |
| 5 | 9.3 | 6.2 |
| 6 | 11.0 | 22.8 |
| 7 | 11.5 | 3.5 |
| 8 | 12.2 | 12.6 |
| 9 | 14.1 | 54.0 |
| 10 | 14.4 | 21.4 |
| 11 | 15.4 | 12.4 |
| 12 | 15.7 | 9.7 |
| 13 | 16.9 | 2.4 |
| 14 | 18.0 | 2.9 |
| 15 | 18.7 | 30.5 |
| 16 | 20.0 | 10.2 |
| 17 | 20.9 | 2.4 |
| 18 | 21.8 | 5.3 |
| 19 | 22.2 | 4.7 |
| 20 | 22.6 | 3.3 |
| 21 | 23.3 | 3.1 |
| 22 | 25.0 | 7.2 |
| 23 | 25.7 | 3.4 |
| 24 | 27.8 | 8.6 |
| 25 | 28.5 | 8.6 |
| 26 | 30.1 | 2.9 |

Further, in some embodiments of the present disclosure, the XRPD pattern of the above-mentioned crystal form VIII of Compound 1 is substantially as shown in FIG. 27.

The DSC curve of the above-mentioned crystal form VIII of Compound 1 has starting points of endothermic peaks at 44.8±3° C., 132.8±3° C., and 323.6±3° C., and a starting point of an exothermic peak at 255.7±3° C.

Further, in some embodiments of the present disclosure, the DSC pattern of the above-mentioned crystal form VIII of Compound 1 is substantially as shown in FIG. 28.

The TGA curve of the above-mentioned crystal form VIII of Compound 1 exhibits a weight loss of 12.15±1% at 200° C.

Further, in some embodiments of the present disclosure, the TGA pattern of the above-mentioned crystal form VIII of Compound 1 is substantially as shown in FIG. 29.

The ninth object of the present disclosure is to provide an active pharmaceutical ingredient (API) comprising at least one of the crystal form I to the crystal form VIII of Compound 1 of the present disclosure. Based on the above-mentioned beneficial effects of the crystal form I to the crystal form VIII of Compound 1 of the present disclosure, the API comprising the crystal form also exhibits beneficial effects substantially consistent with those of the crystal form (e.g., stability, water solubility, etc.). In particular, the API can be Compound 1, or WX-216 and/or other salt forms of WX-216, wherein the other salt forms of WX-216 can be common pharmaceutical salts in the art, including but not limited to, salts formed with bases, such as, potassium salt, calcium salt, magnesium salt, triethylamine salt, etc.; and salts formed with acids, such as, chloride, sulfate, phosphate, methanesulfonate, benzenesulfonate, p-toluenesulfonate, etc. More specially, the mass percent of Compound I and/or Compound II and/or Compound III and/or Compound IV and/or Compound V and/or Compound VI and/or Compound VII and/or Compound VIII contained in the API is any value in a range of 0.01-99.99%. Further, the mass percent of Compound I and/or Compound II and/or Compound III and/or Compound IV and/or Compound V and/or Compound VI and/or Compound VII and/or Compound VIII contained in the API is any value in a range of 1.00-99.00%.

The tenth object of the present disclosure is to provide a pharmaceutical composition consisting of the above-mentioned API and pharmaceutically acceptable excipients. The pharmaceutically acceptable excipients include, but are not limited to, at least one of fillers, binders, disintegrants, lubricants, etc. In particular, the beneficial effects of the above-mentioned crystal forms I to VIII of Compound 1 of the present disclosure are finally reflected in the pharmaceutical composition. More specially, the mass percent of the API contained in the pharmaceutical composition is any value in a range of 1.00-99.00%. Further, the mass percent of the API contained in the pharmaceutical composition is any value in a range of 5.00-95.00%. Further, the mass percent of the API contained in the pharmaceutical composition is any value in a range of 10.00-90.00%.

In summary, the crystal form I to the crystal form VIII of Compound 1 of the present disclosure have a certain pharmaceutical prospect. Therefore, if it is proved by detection means that the crystal form I to the crystal form VIII of Compound 1 are present in the above-mentioned API and/or pharmaceutical composition, the crystal form I to the crystal form VIII of Compound 1 provided in the present disclosure should be deemed to be used. In addition to the X-ray powder diffraction (XRPD) as described above, the detection means can further include differential scanning calorimetry (DSC), infrared spectroscopy (IR), Raman spectroscopy (Raman), solid state nuclear magnetic resonance (SSNMR), and any other methods which can demonstrate, alone or in combination, the use of the crystal form I to the crystal form VIII of Compound 1 of the present disclosure. In addition, influence caused by pharmaceutical excipients can be removed by methods commonly used by those skilled in the art, e.g., a subtractive mapping method.

The present disclosure has the following advantages and beneficial effects compared with the prior art:

1. The present disclosure first discloses Compound 1, a sodium salt of WX-216, of which the advantage in solubility compared with WX-216 exceeds a reasonable prediction of those skilled in the art;
2. The present disclosure first discloses the crystal form I of Compound 1 and the method of preparing the same, wherein the crystal form has characteristics of high stability, and has a considerable pharmaceutical prospect;
3. The present disclosure first discloses the crystal form II of Compound 1 and the method of preparing the same, wherein the crystal form has characteristics of high stability, and has a considerable pharmaceutical prospect;
4. The present disclosure first discloses the crystal form III of Compound 1 and the method of preparing the same, wherein the crystal form has characteristics of high stability, and has a considerable pharmaceutical prospect;
5. The present disclosure first discloses the crystal form IV of Compound 1 and the method of preparing the same, wherein the crystal form has characteristics of high stability, and has a considerable pharmaceutical prospect;
6. The present disclosure first discloses the crystal form V of Compound 1 and the method of preparing the same, wherein the crystal form has characteristics of high stability, and has a considerable pharmaceutical prospect;
7. The present disclosure first discloses the crystal form VI of Compound 1 and the method of preparing the same, which provides a variety of options of intermediate products and/or APIs for large-scale production of APIs and the downstream process of pharmaceutical products (e.g., pharmaceutical process);
8. The present disclosure first discloses the crystal form VII of Compound 1 and the method of preparing the same, wherein the crystal form has characteristics of high stability, and has a considerable pharmaceutical prospect;
9. The present disclosure first discloses the crystal form VIII of Compound 1 and the method of preparing the same, wherein the crystal form has characteristics of high stability, and has a considerable pharmaceutical prospect;
10. The present disclosure provides an API comprising at least one of the crystal form I to the crystal form VIII of Compound 1 of the present disclosure, which exhibits beneficial effects substantially consistent with those of the crystal form I to the crystal form VIII of Compound 1 of the present disclosure;
11. The present disclosure provides a pharmaceutical composition consisting of the API of the present disclosure and pharmaceutically acceptable excipients, which has beneficial effects substantially consistent with those of the crystal form I to the crystal form VIII of Compound 1 of the present disclosure.

DETAILED DESCRIPTION

Hereinafter the present disclosure is further described in details below by reference to the examples and the drawings, but the embodiments of the present disclosure are not limited thereto.

Detection Conditions

X-Ray Powder Diffraction
X-Ray powder diffractometer: Bruker D8 Advance;
2θ Scanning angle: from 3° to 45°;
Scanning Step: 0.02°;
Exposure time: 0.2 second;
Voltage and current of light pipe: 40 KV, 40 mA.

Differential Scanning Calorimetric Analysis
Differential scanning calorimetric analyzer: TA Discovery 2500 (TA, US);
Heating rate: 10° C./min;
Test method: Sample was precisely weighed, placed into a DSC Tzero sample disk, and heated to 350° C. The purging rate of nitrogen in the furnace was 50 mL/min.

Thermogravimetric Analysis
Thermogravimetric analyzer: TA Discovery 55 (TA, US);
Test method: Sample was placed in an equilibrated aluminum sample disk, and automatically weighed in a heating furnace. The sample was heated at a rate of 10° C./min to 400° C. The purging rate of nitrogen was 60 mL/min at the site of the sample, and 40 mL/min at the site of balance.

Example 1. Preparation Method of Compound 1

WX-216 was prepared in accordance with the method disclosed in Example 4 of the patent WO2018041263.

5 g of WX-216 was added into a 250 mL eggplant-shaped flask, and THF (100 mL) and NaOH (aq., 0.477 g in 1 mL of water) were added. The mixture was stirred at 30° C. for 12 hrs. The solids were filtered, and the filter cake was dried under vacuum at 40° C. to give Compound 1.

Example 2. Preparation Method of Crystal Form I of Compound 1

Figure 1:
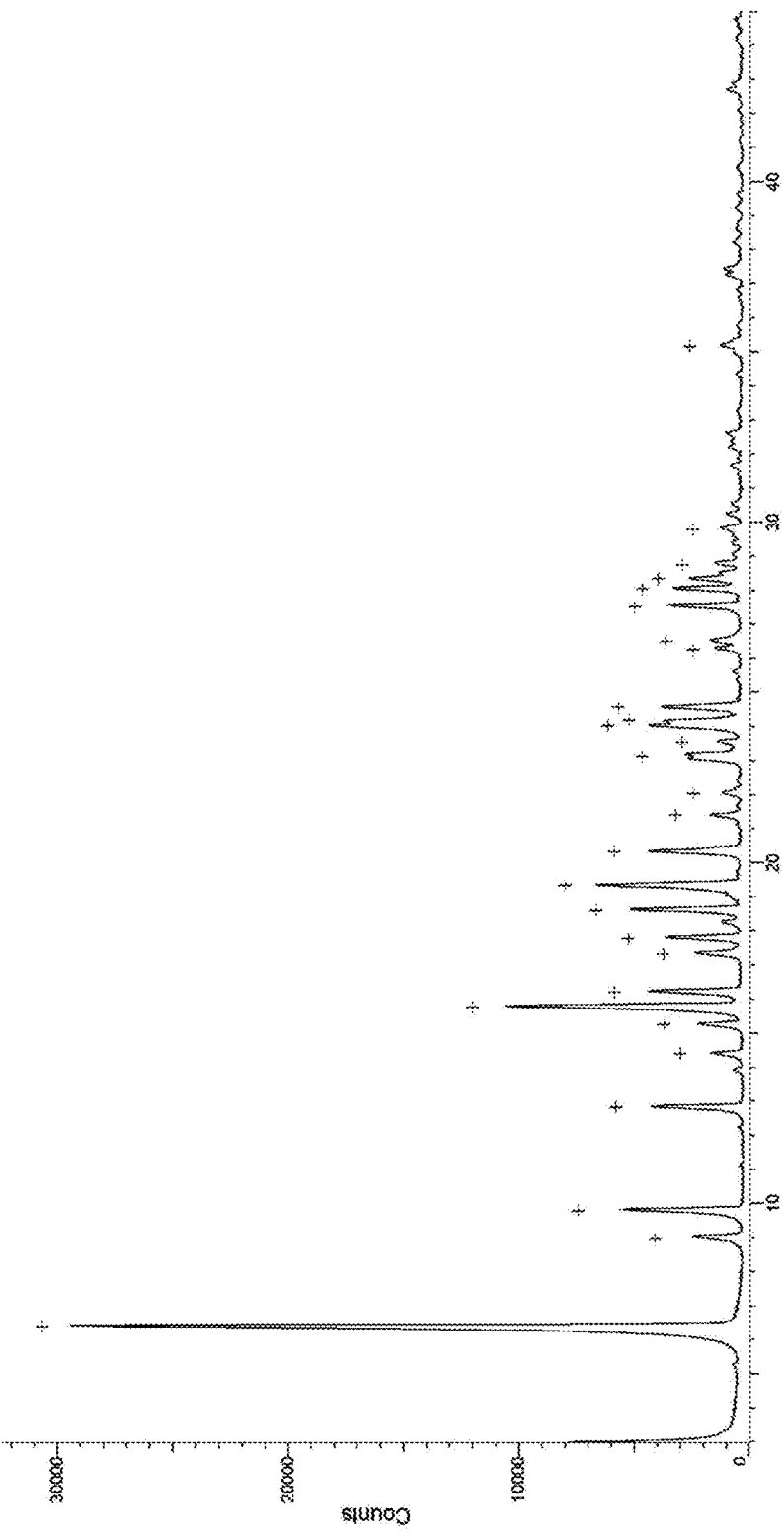
FIG. 1: the XRPD pattern of the crystal form I of Compound 1.
Figure 2:
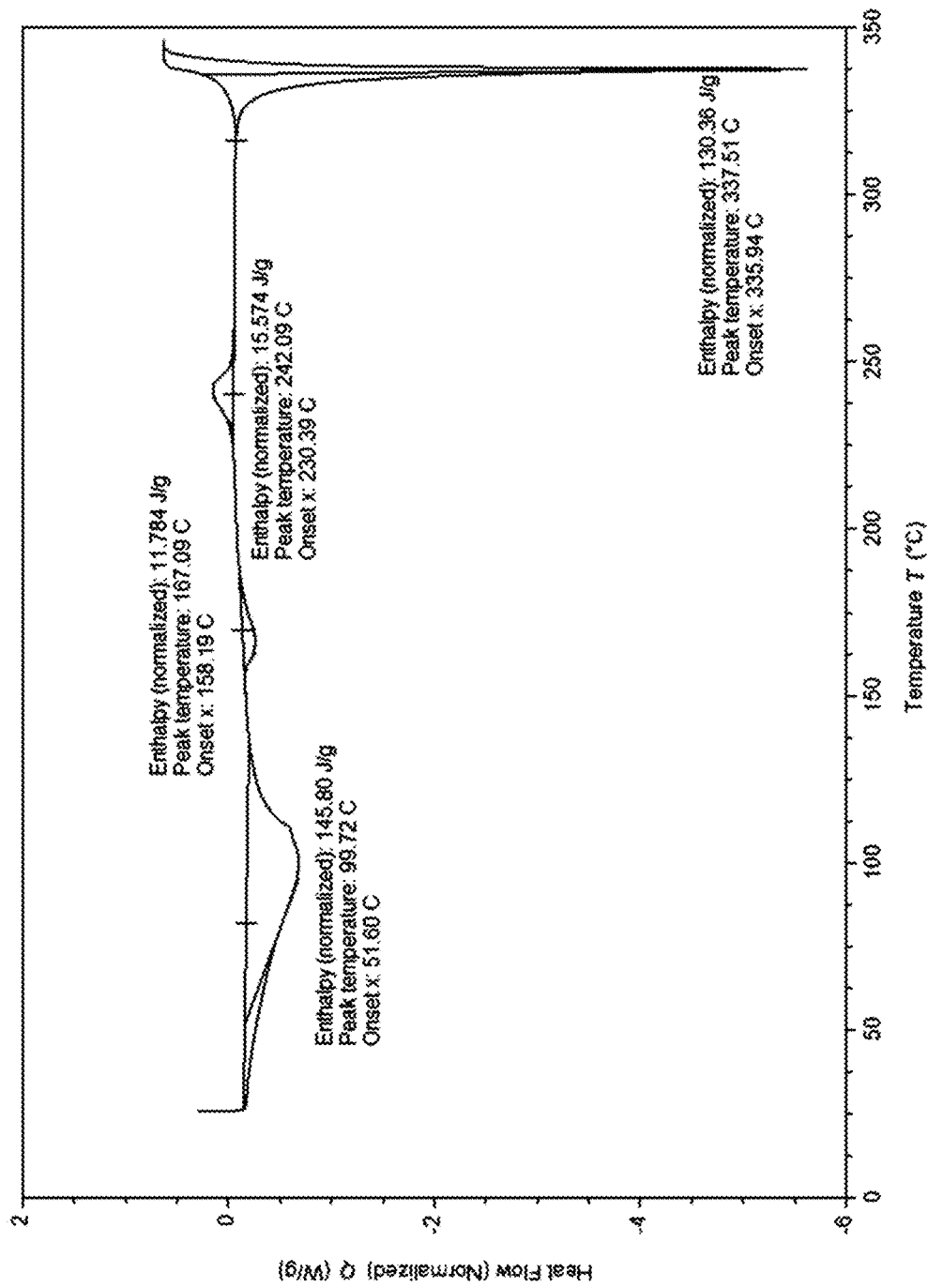
FIG. 2: the DSC pattern of the crystal form I of Compound 1.
Figure 3:
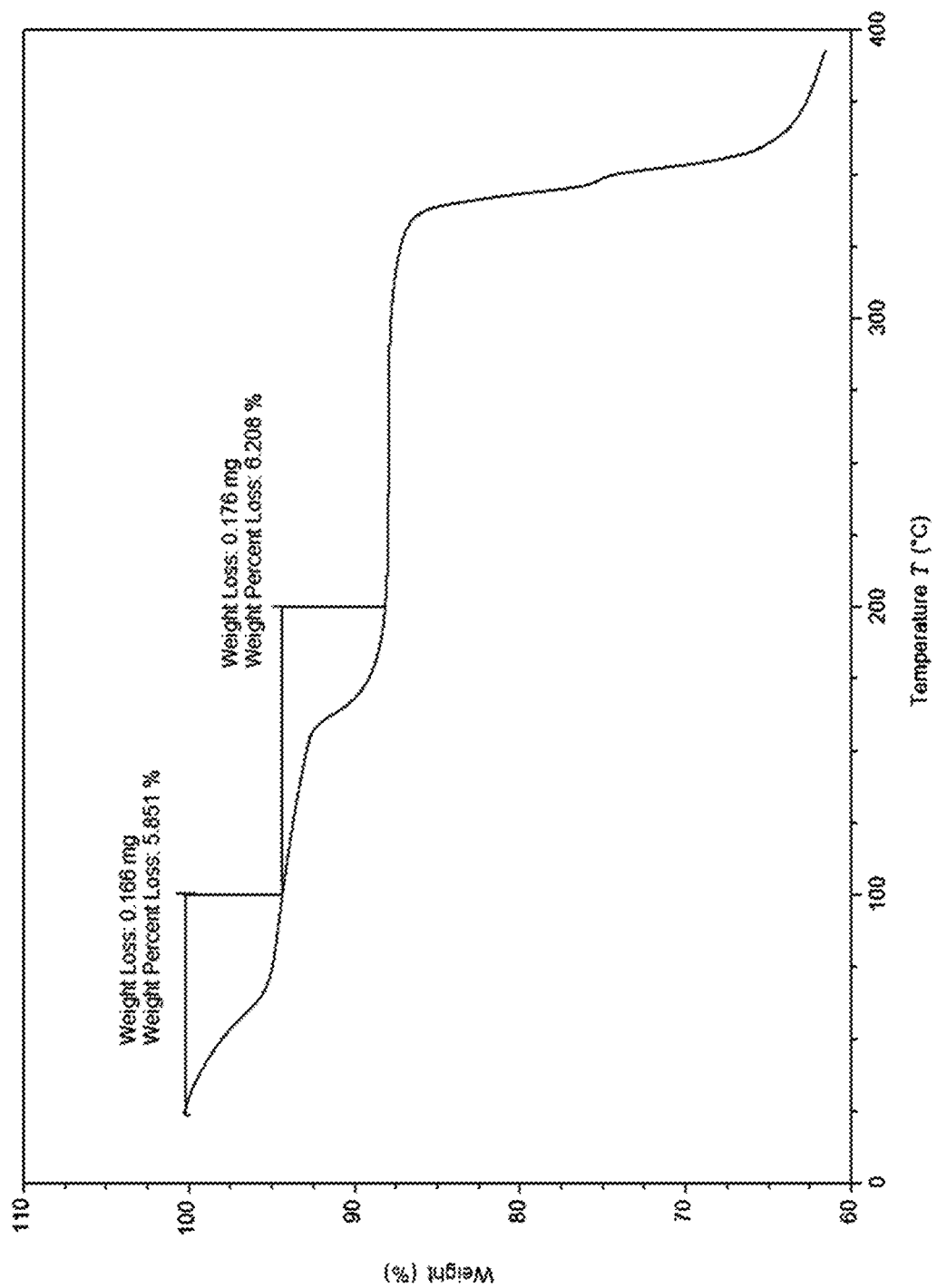
FIG. 3: the TGA pattern of the crystal form I of Compound 1.

10 mg of Compound 1 prepared in accordance with the method of Example 1 was weighed and suspended in 1 mL of acetone. 150 μL of solvent was added dropwise at 60° C. until the solid was completely dissolved. Then, the mixture was cooled to room temperature, stirred for 3 hrs, and then centrifuged for solid-liquid separation. The solid was dried under vacuum at room temperature to give the crystal form I of Compound 1. The obtained crystal form I has an XRPD pattern as shown in FIG. 1, a DSC pattern as shown in FIG. 2, and a TGA pattern as shown in FIG. 3.

Example 3. Preparation Method of Crystal Form I of Compound 1

An appropriate amount of Compound 1 prepared in accordance with the method of Example 1 was weighed and formulated into a saturated solution in ethylene glycol monomethyl ether. 150 μL of the saturated solution was placed at room temperature under the atmosphere of diffusion solvent acetone, and solid was precipitated after 3 days. The mixture was centrifuged for solid-liquid separation. The solid was dried at room temperature under vacuum to give the crystal form I of Compound 1.

Figure 4:
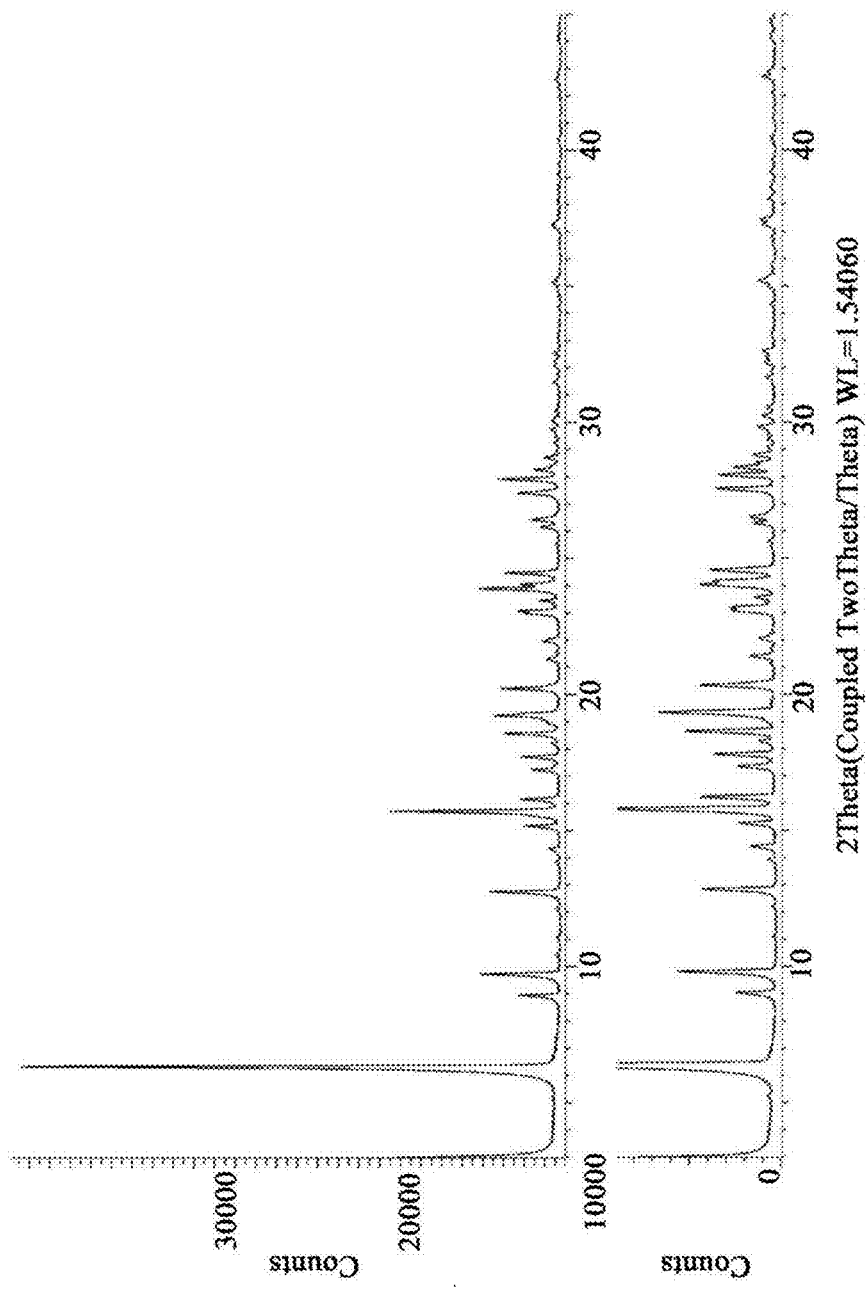
FIG. 4: the XRPD comparison pattern of the crystal form I of Compound 1.

The XRPD comparison pattern of the obtained crystal form I is as shown in FIG. 4.

Example 4. Preparation Method of Crystal Form II of Compound 1

Figure 5:
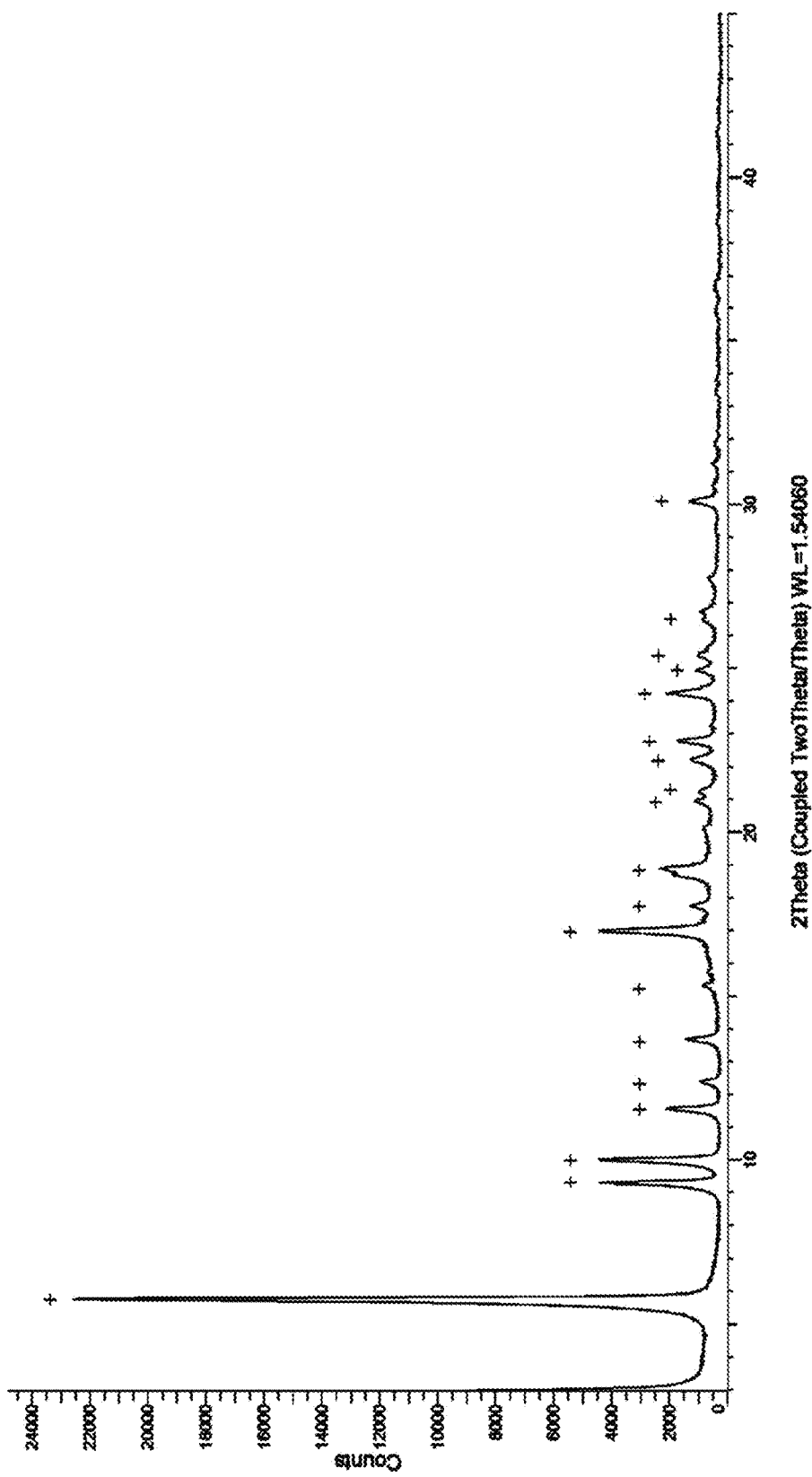
FIG. 5: the XRPD pattern of the crystal form II of Compound 1.
Figure 6:
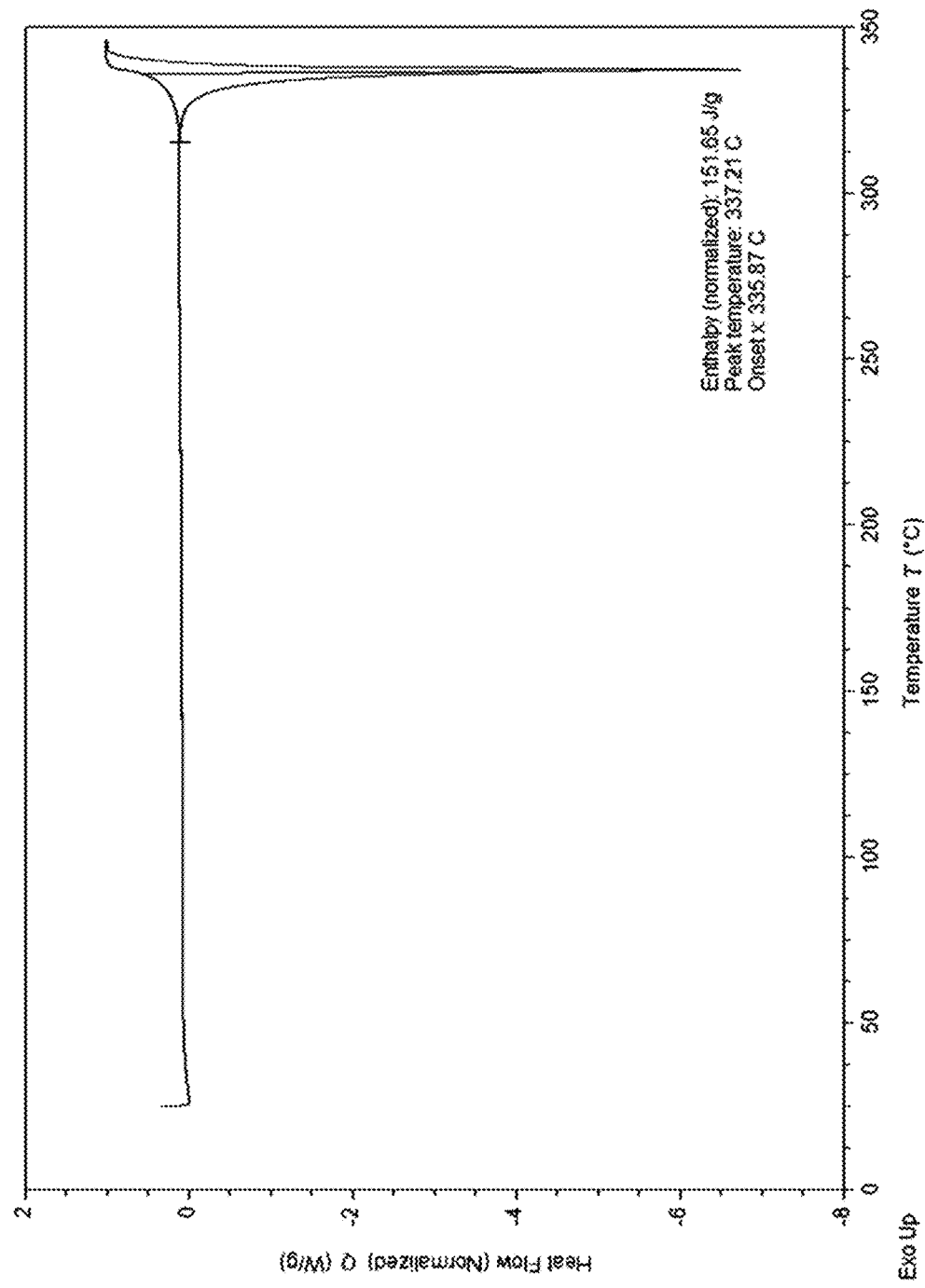
FIG. 6: the DSC pattern of the crystal form II of Compound 1.
Figure 7:
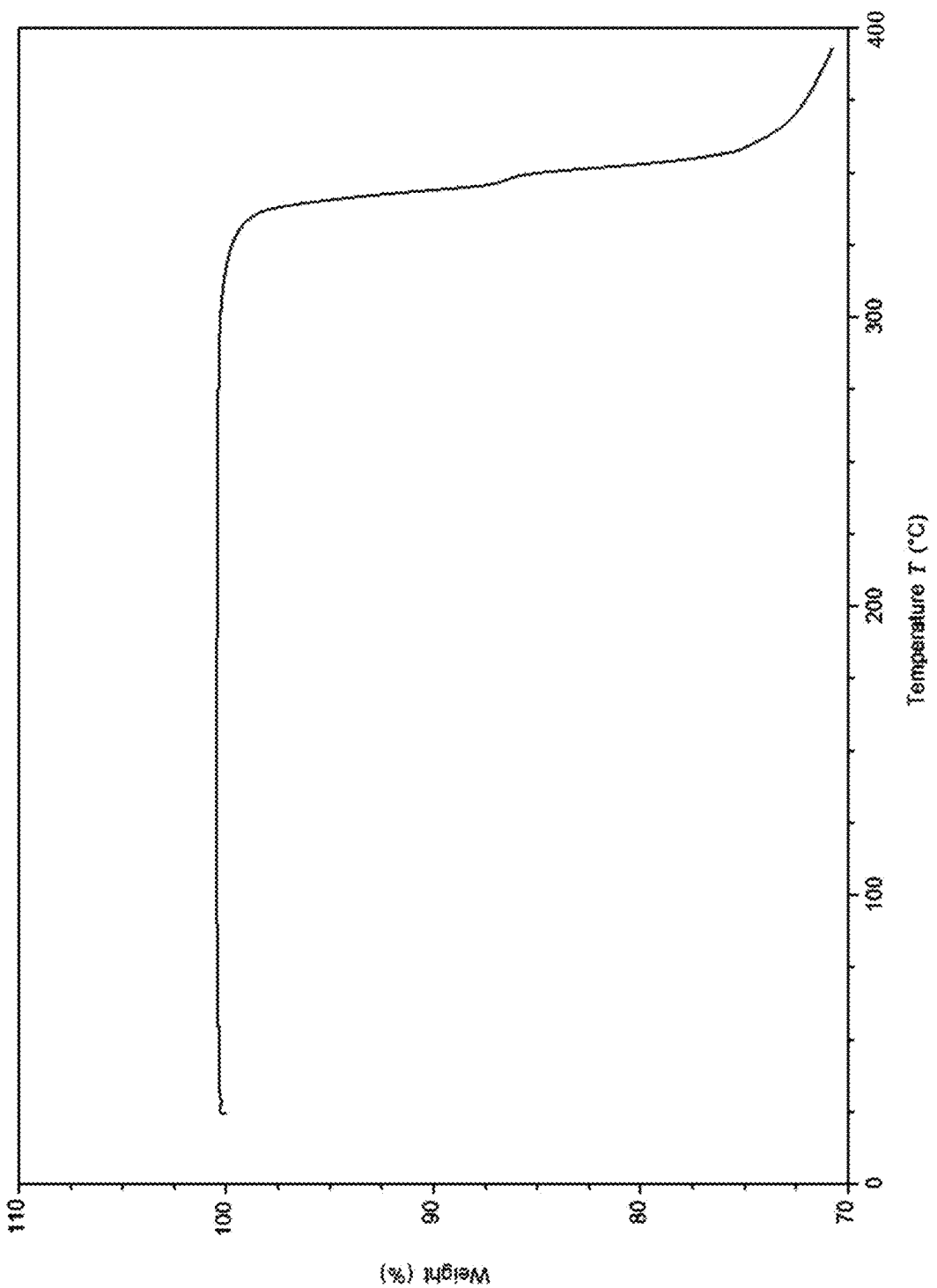
FIG. 7: the TGA pattern of the crystal form II of Compound 1.

10 mg of the crystal form I of Compound 1 prepared in accordance with the method of Example 2 was weighed and placed in a platinum crucible, heated at a rate of 10° C./min to 300° C. for 0.5 minute, and air-cooled to room temperature to give the crystal form II of Compound 1. The obtained crystal form II has an XRPD pattern as shown in FIG. 5, a DSC pattern as shown in FIG. 6, and a TGA pattern as shown in FIG. 7.

Example 5. Preparation Method of Crystal Form II of Compound 1

An appropriate amount of Compound 1 prepared in accordance with the method of Example 1 was weighed and formulated to a saturated solution in dimethylformamide. 150 μL of the saturated solution was placed at room temperature under an atmosphere of diffusion solvent acetone, and solid was precipitated after 3 days. The mixture was centrifuged for solid-liquid separation. The solid was dried at room temperature under vacuum to give the crystal form II of Compound 1.

Figure 8:
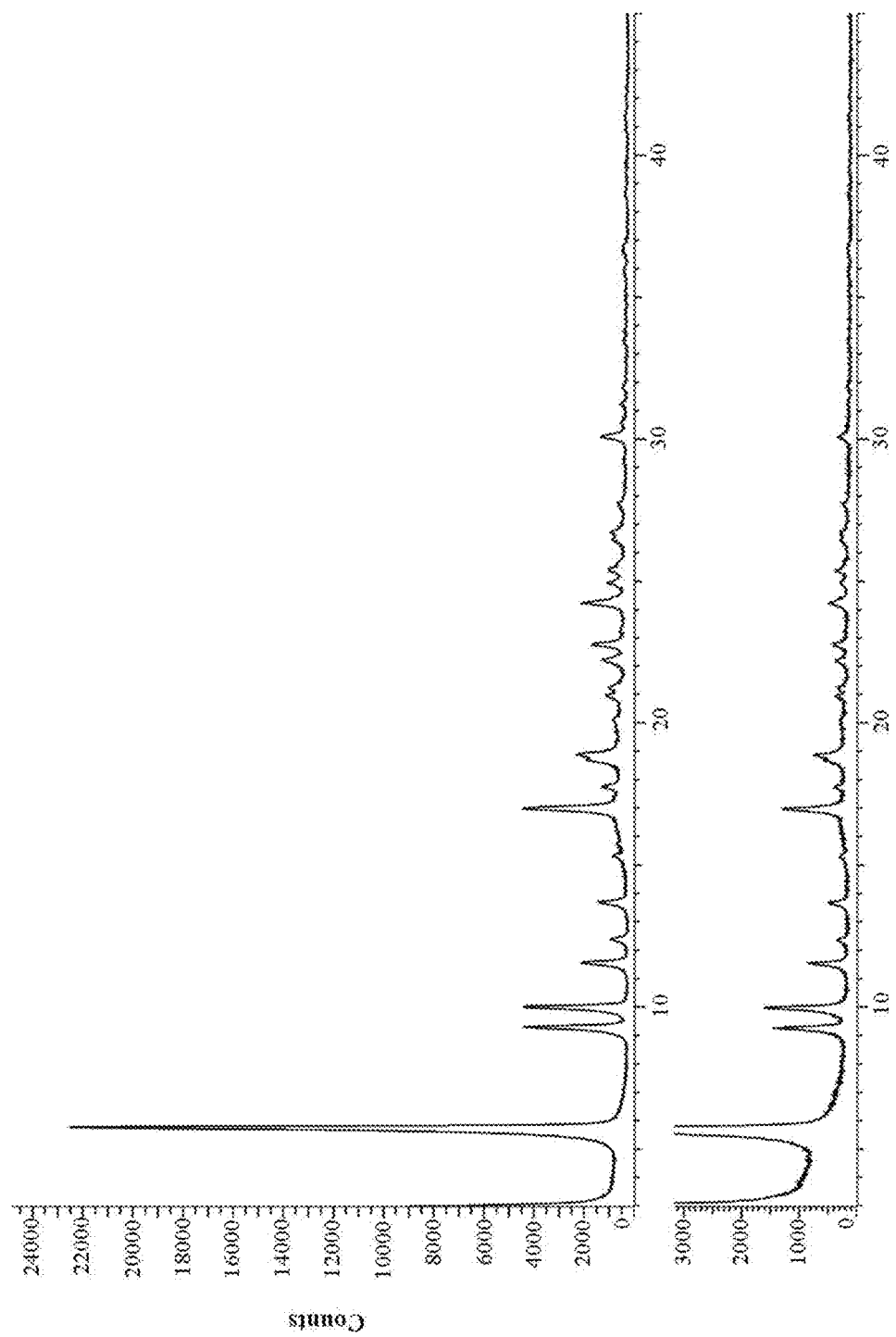
FIG. 8: the XRPD comparison pattern of the crystal form II of Compound 1.

The XRPD comparison pattern of the crystal form II is as shown in FIG. 8.

Example 6. Preparation Method of Crystal Form III of Compound 1

Figure 9:
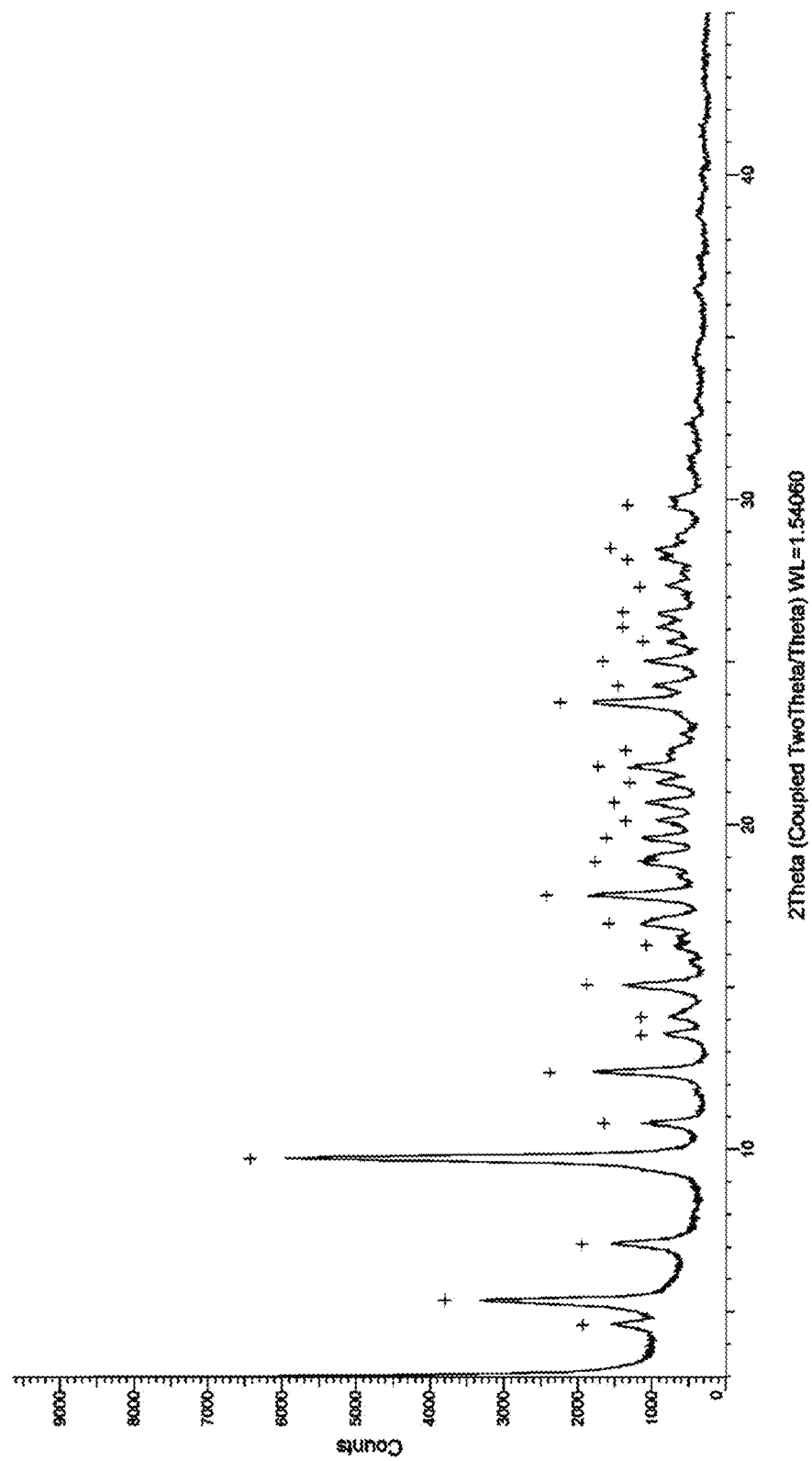
FIG. 9: the XRPD pattern of the crystal form III of Compound 1.
Figure 10:
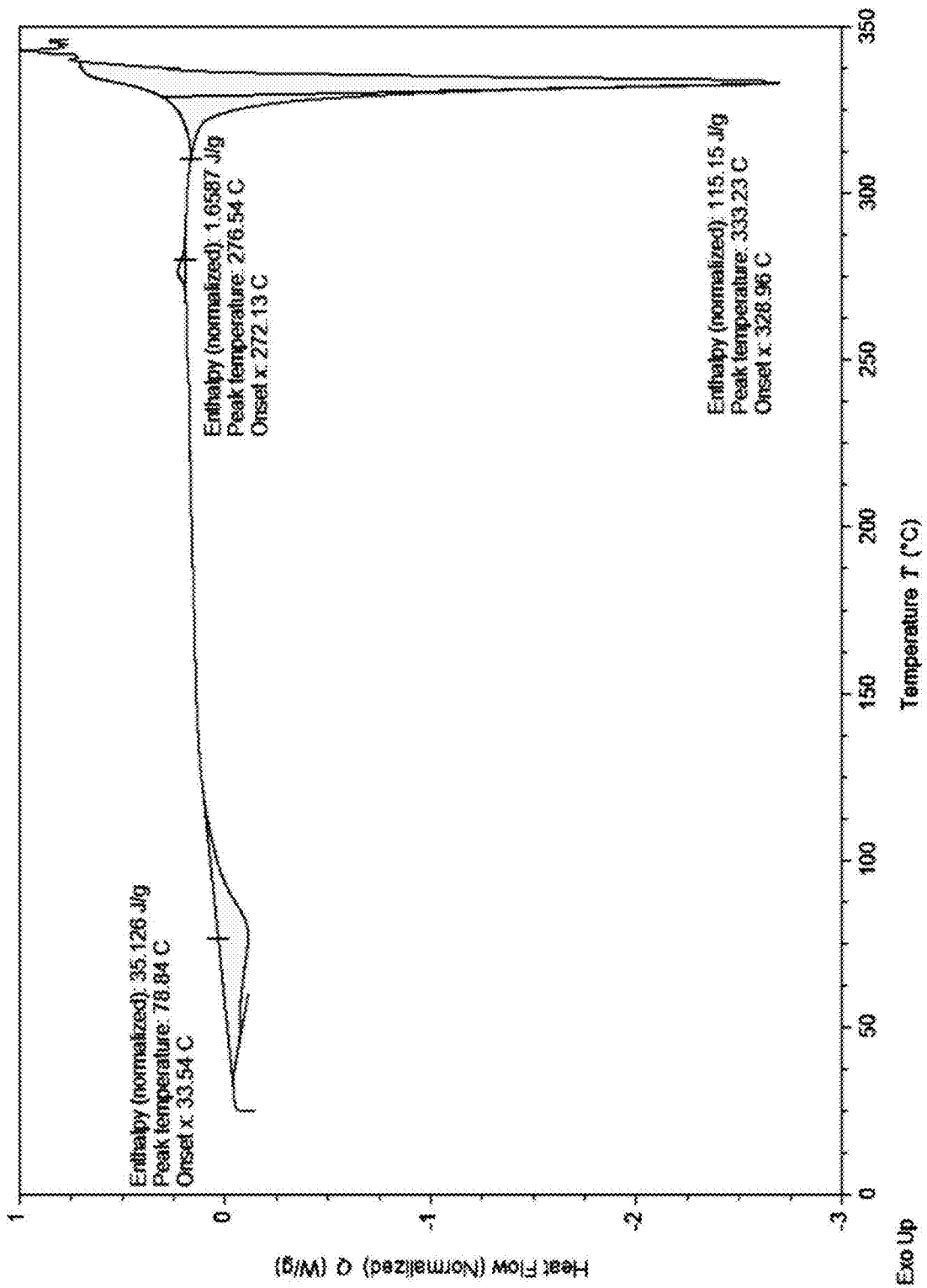
FIG. 10: the DSC pattern of the crystal form III of Compound 1.
Figure 11:
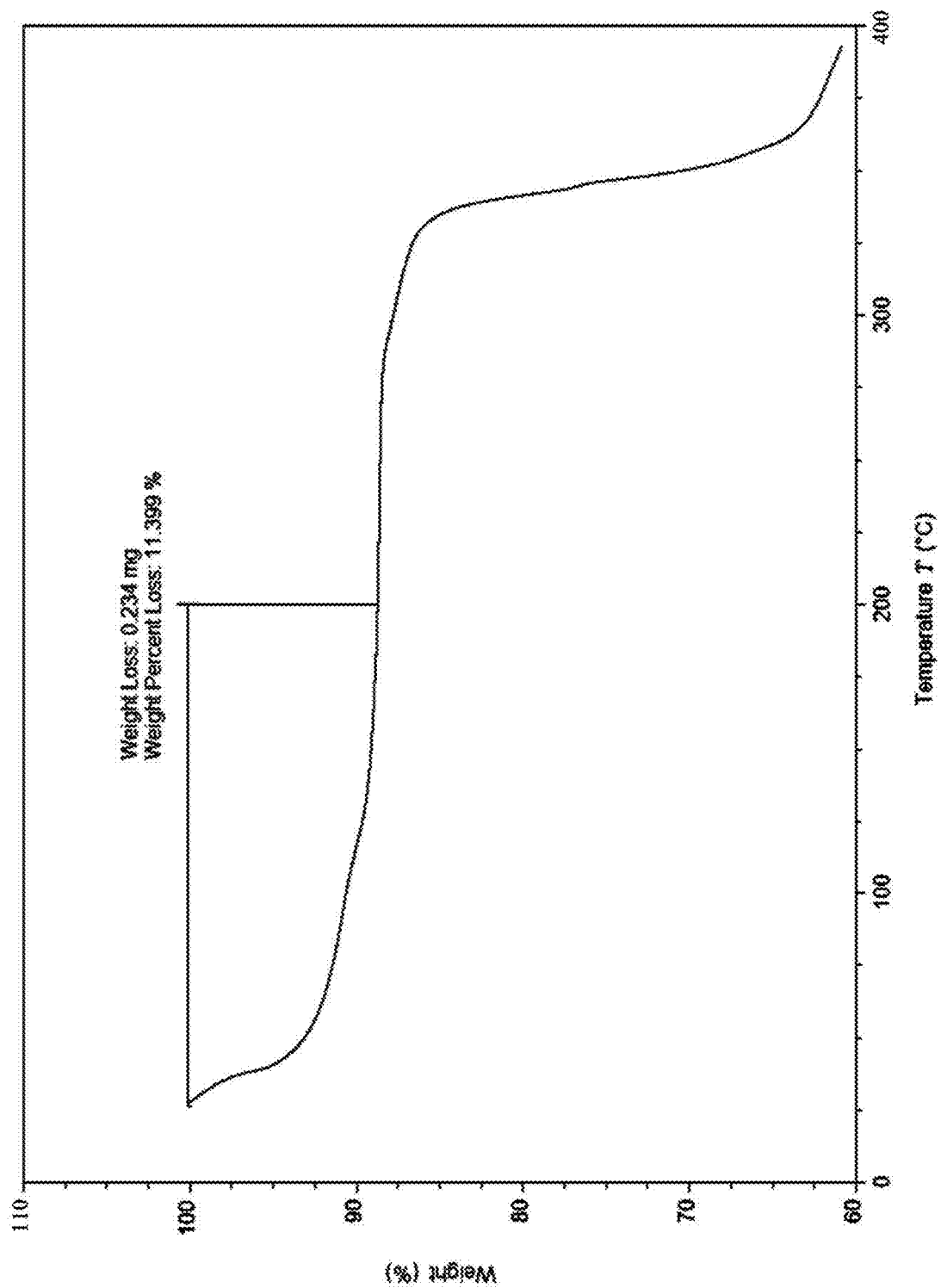
FIG. 11: the TGA pattern of the crystal form III of Compound 1.

80 mg of the crystal form I of Compound 1 prepared in accordance with the method of Example 2 was weighed and placed in 3.5 mL of pure water. The suspension was stirred at 60° C. for 19 hrs, and then filtered. The filter cake was dried at room temperature under vacuum to give the crystal form III of Compound 1. The obtained crystal form III has an XRPD pattern as shown in FIG. 9, a DSC pattern as shown in FIG. 10, and a TGA pattern as shown in FIG. 11.

Example 7. Preparation Method of Crystal Form III of Compound 1

500 mg of the crystal form I of Compound 1 prepared by the method of Example 2 was weighed and added into a mixed solution of 1.5 mL of ethanol and 7.5 mL of water, suspended and slurried at 60° C. for 4 hrs, cooled to room temperature and filtered, and dried at room temperature under vacuum to give the crystal form III of Compound 1.

Figure 12:
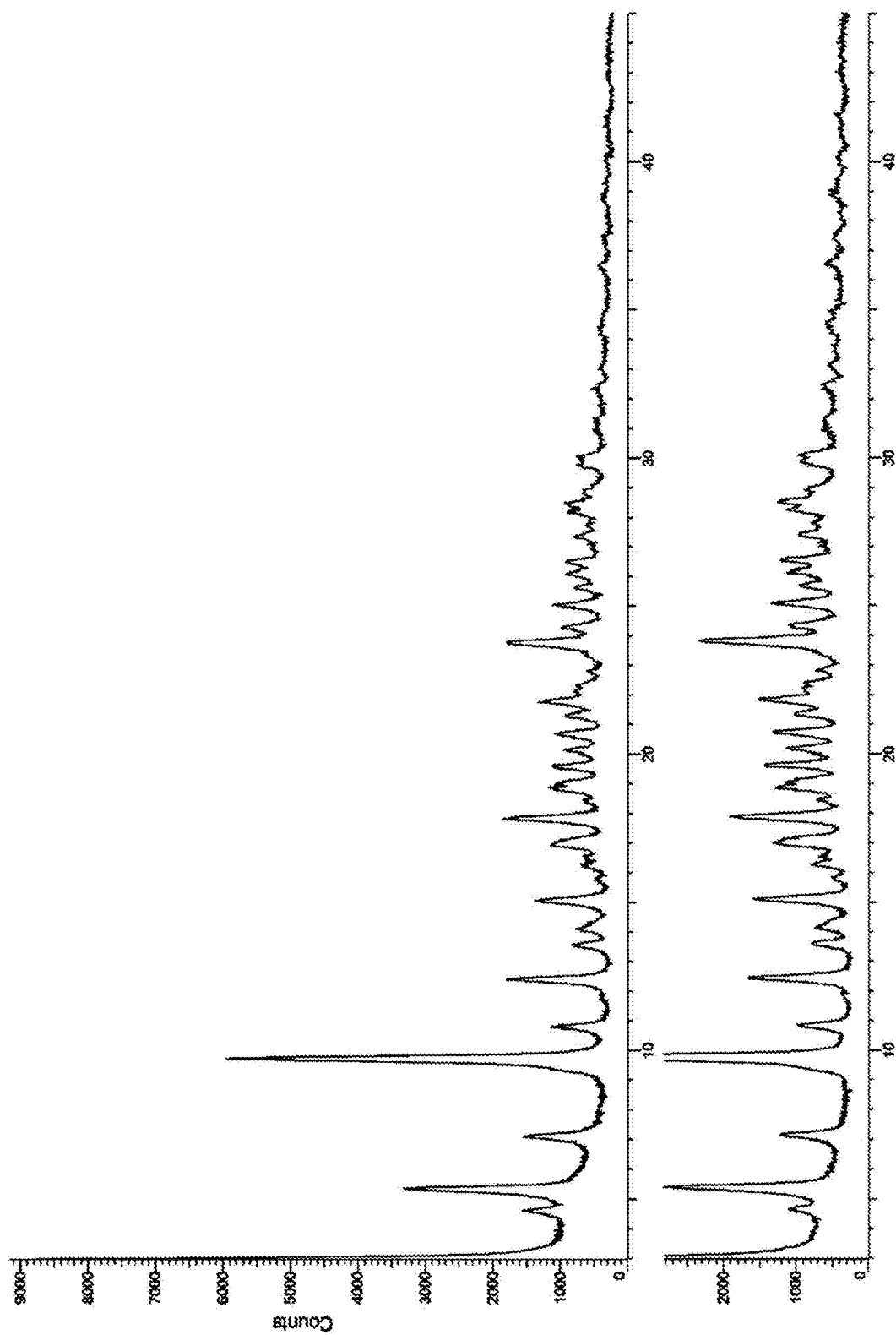
FIG. 12: the XRPD comparison pattern of the crystal form III of Compound 1.

The XRPD comparison pattern of the crystal form III is as shown in FIG. 12.

Example 8. Preparation Method of Crystal Form IV of Compound 1

Figure 13:
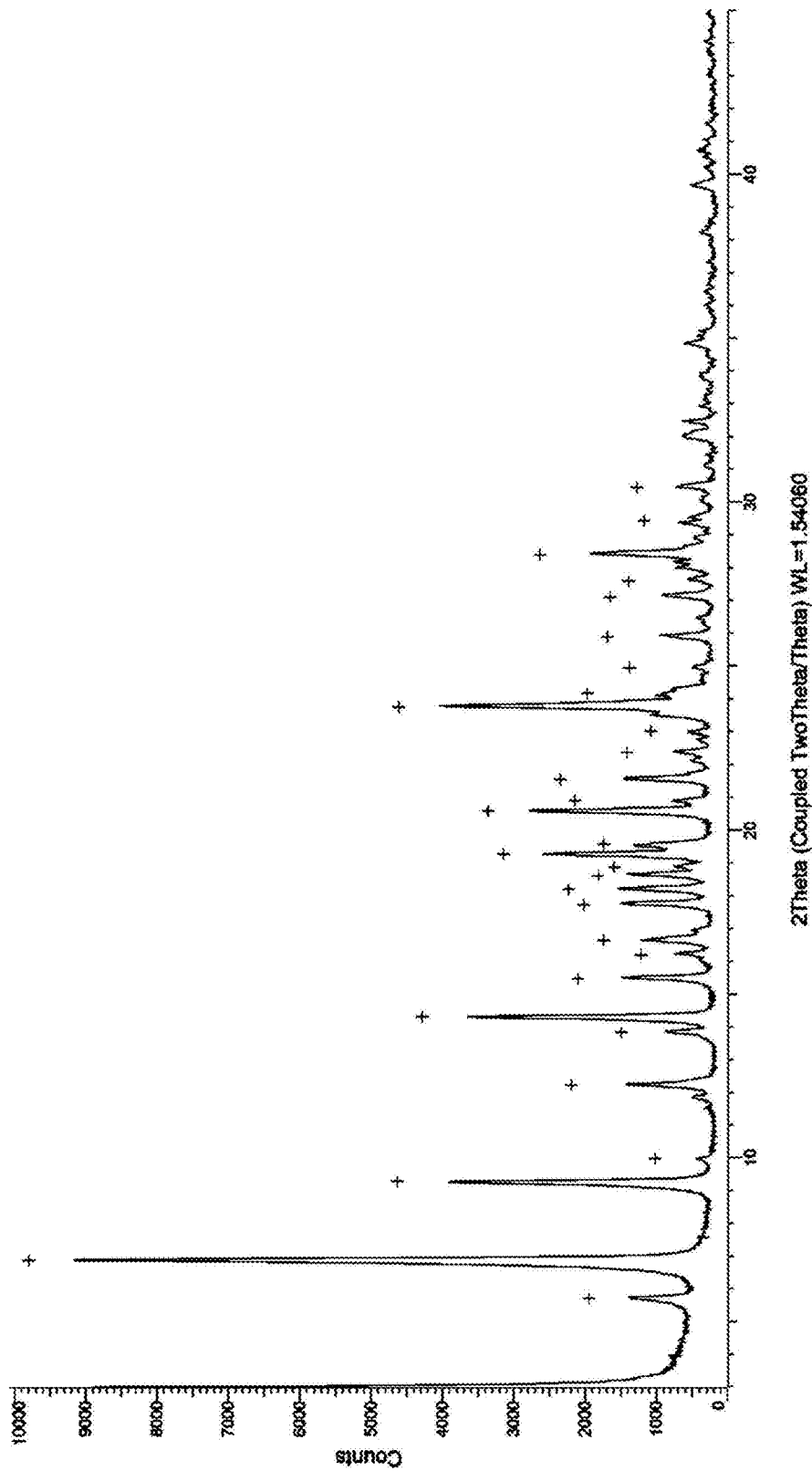
FIG. 13: the XRPD pattern of the crystal form IV of Compound 1.
Figure 14:
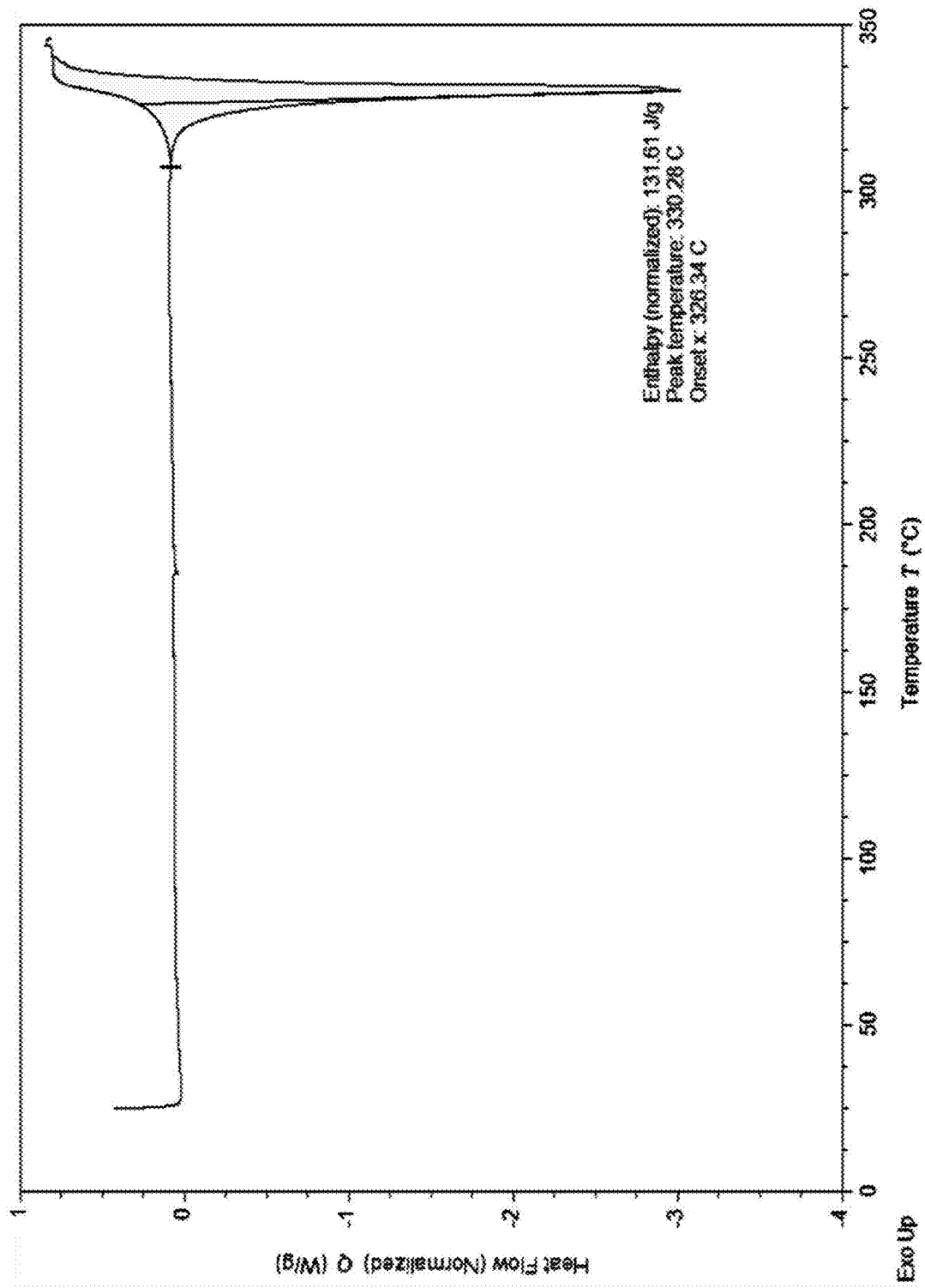
FIG. 14: the DSC pattern of the crystal form IV of Compound 1.
Figure 15:
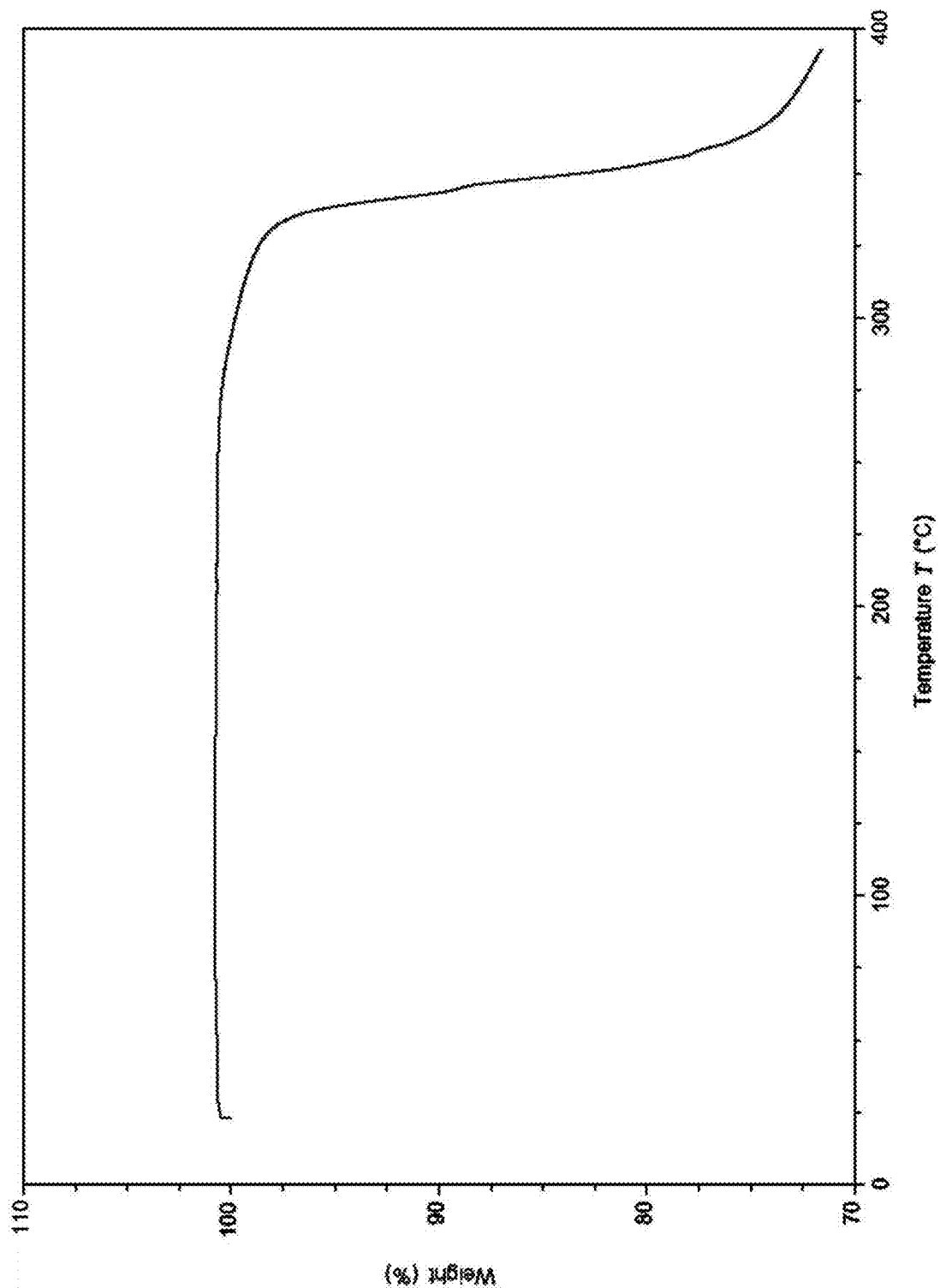
FIG. 15: the TGA pattern of the crystal form IV of Compound 1.

10 mg of the crystal form III of Compound 1 prepared in accordance with the method of Example 6 was weighed and placed in a platinum crucible, heated at a rate of 10° C./min to 280° C. for 0.5 minute, and air-cooled to room temperature to give the crystal form IV of Compound 1. The obtained crystal form IV has an XRPD pattern as shown in FIG. 13, a DSC pattern as shown in FIG. 14, and a TGA pattern as shown in FIG. 15.

Example 9. Preparation Method of Crystal Form V of Compound 1

Figure 16:
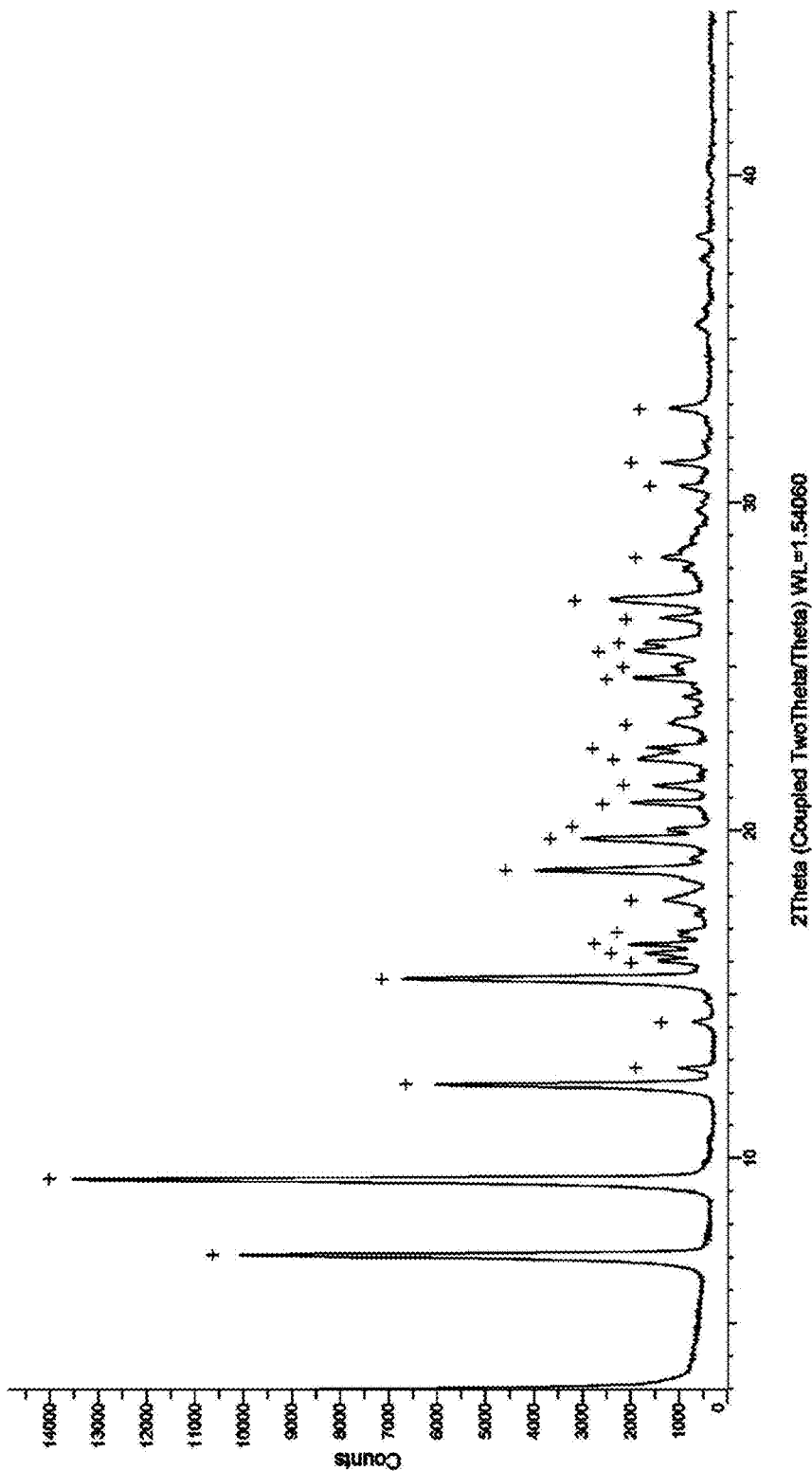
FIG. 16: the XRPD pattern of the crystal form V of Compound 1.
Figure 17:
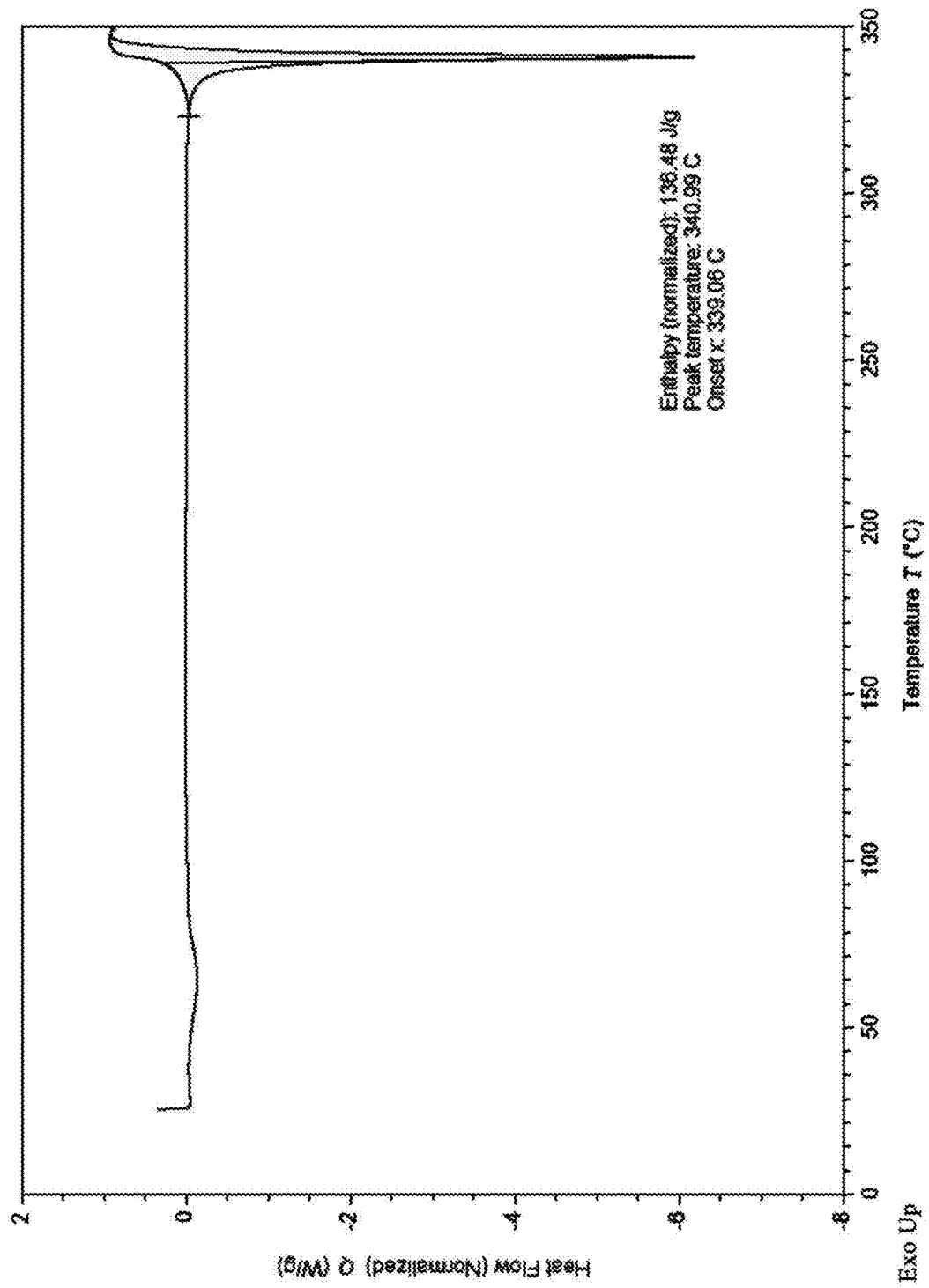
FIG. 17: the DSC pattern of the crystal form V of Compound 1.
Figure 18:
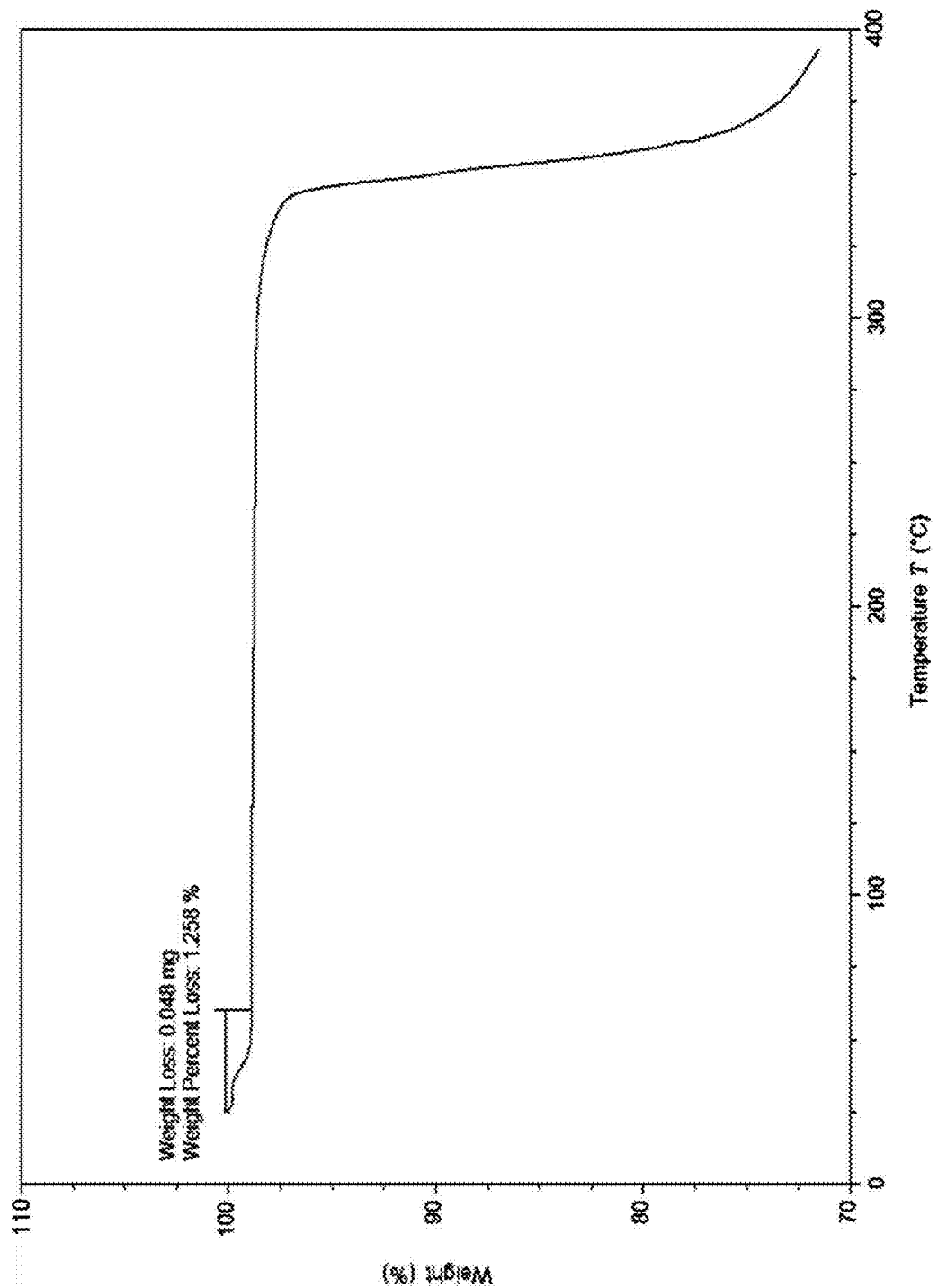
FIG. 18: the TGA pattern of the crystal form V of Compound 1.

An appropriate amount of Compound 1 prepared in accordance with the method of Example 1 was dissolved in methanol to prepare a saturated solution. 200 μL of the prepared saturated solution was added dropwise into 1.5 mL of iso-propyl acetate at room temperature. The mixture was stirred at room temperature for 19 hrs, and then centrifuged for solid-liquid separation. The solid was dried under vacuum at room temperature to give the crystal form V of Compound 1. The obtained crystal form V has an XRPD pattern as shown in FIG. 16, a DSC pattern as shown in FIG. 17, and a TGA pattern as shown in FIG. 18.

Example 10. Preparation Method of Crystal Form V of Compound 1

An appropriate amount of Compound 1 prepared in accordance with the method of Example 1 was weighed and formulated into a saturated solution in methanol. 150 μL of the saturated solution was placed at room temperature under the atmosphere of diffusion solvent acetonitrile, and solid was precipitated after 5 days. The mixture was centrifuged for solid-liquid separation. The solid was dried at room temperature under vacuum to give the crystal form V of Compound 1.

Figure 19:
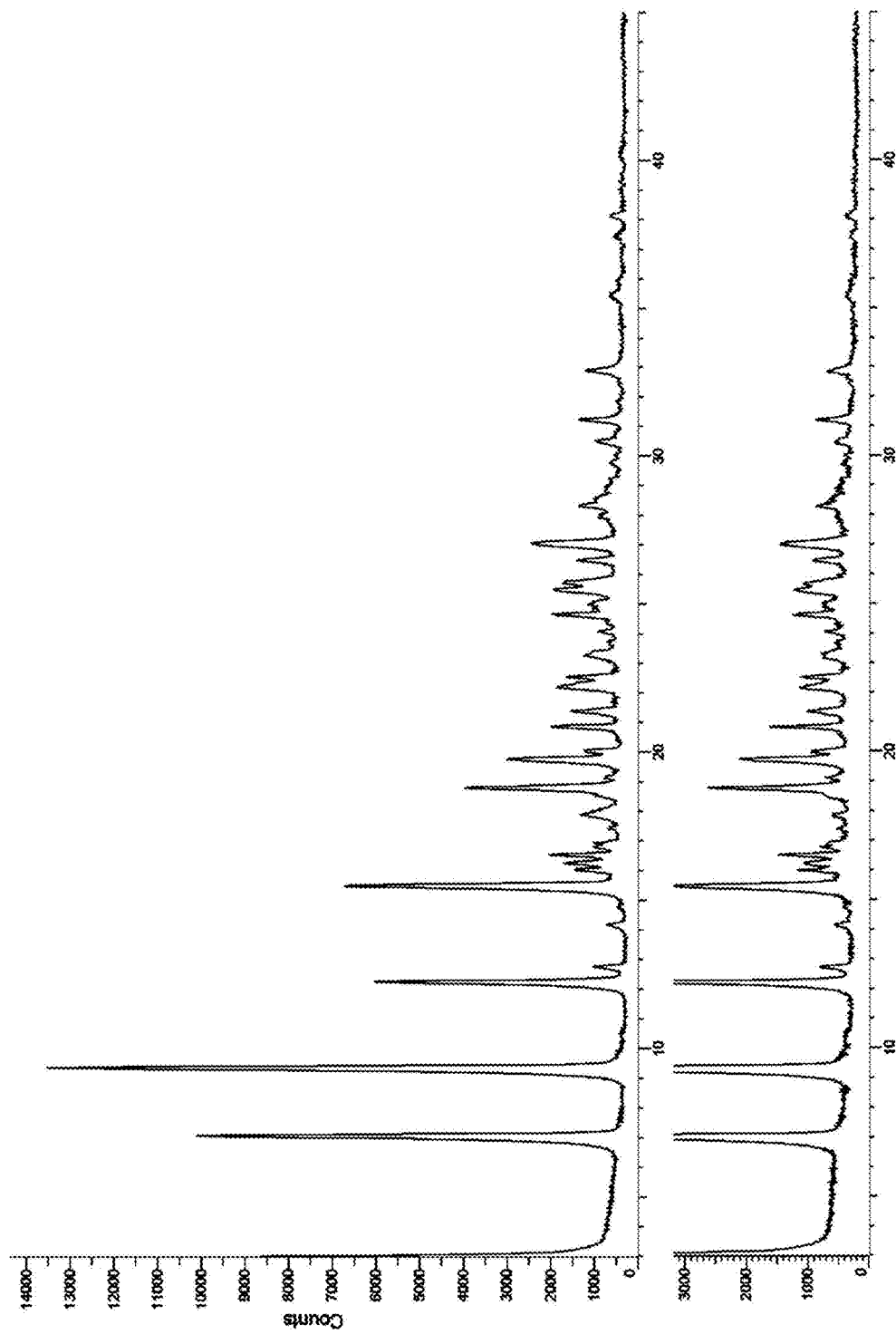
FIG. 19: the XRPD comparison pattern of the crystal form V of Compound 1.

The XRPD comparison pattern of the crystal V is as shown in FIG. 19.

Example 11. Preparation Method of Crystal Form VI of Compound 1

Figure 20:
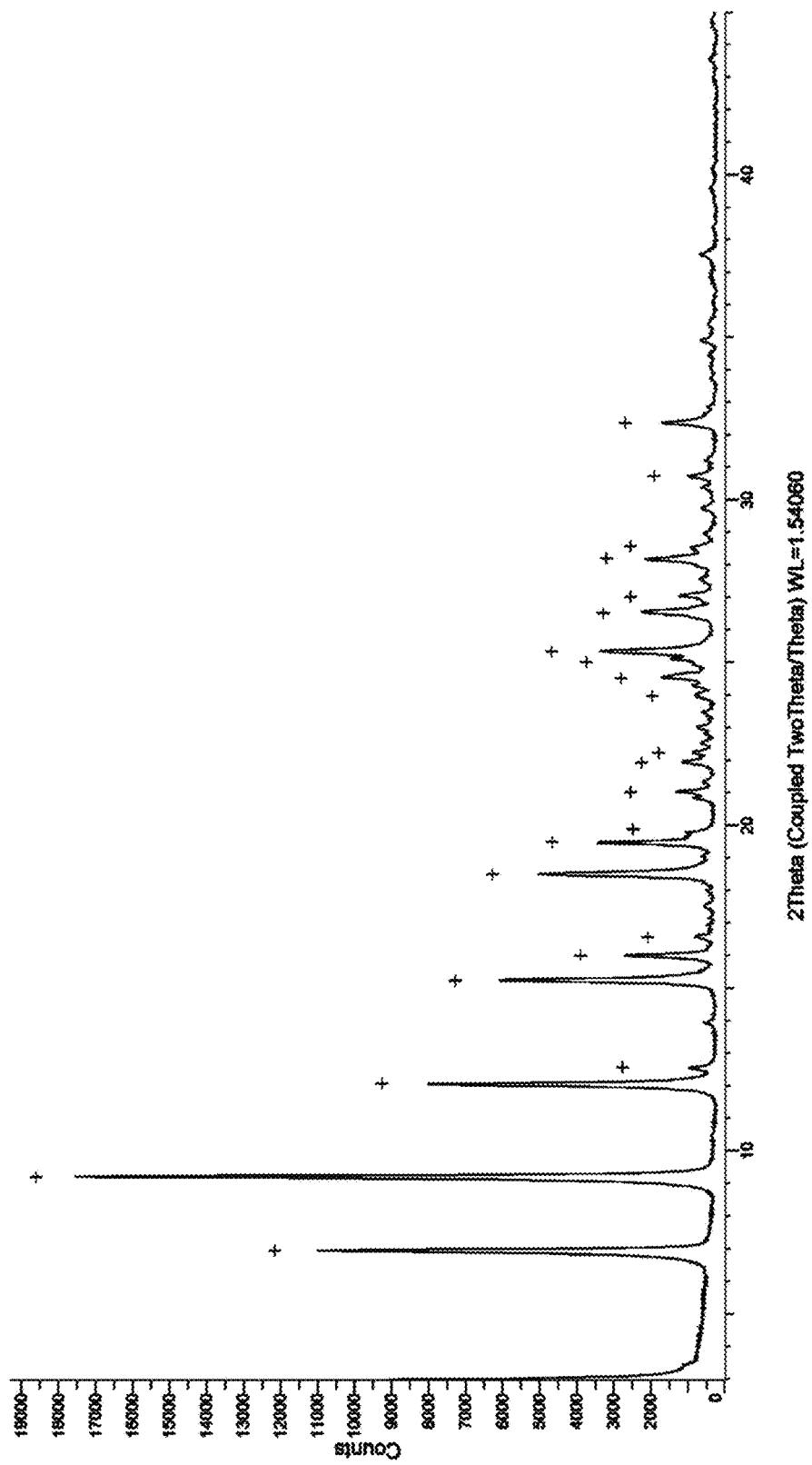
FIG. 20: the XRPD pattern of the crystal form VI of Compound 1.
Figure 21:
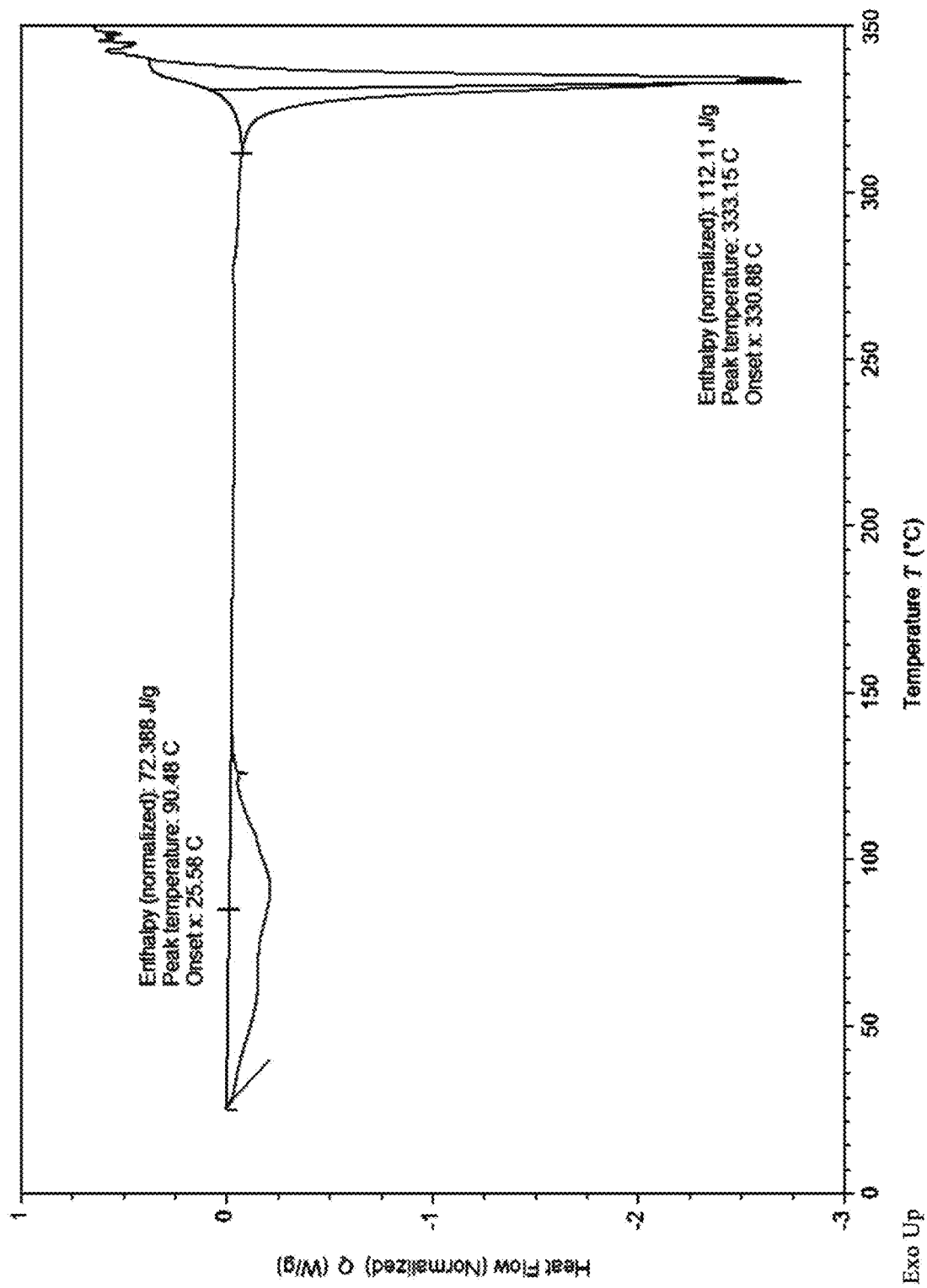
FIG. 21: the DSC pattern of the crystal form VI of Compound 1.
Figure 22:
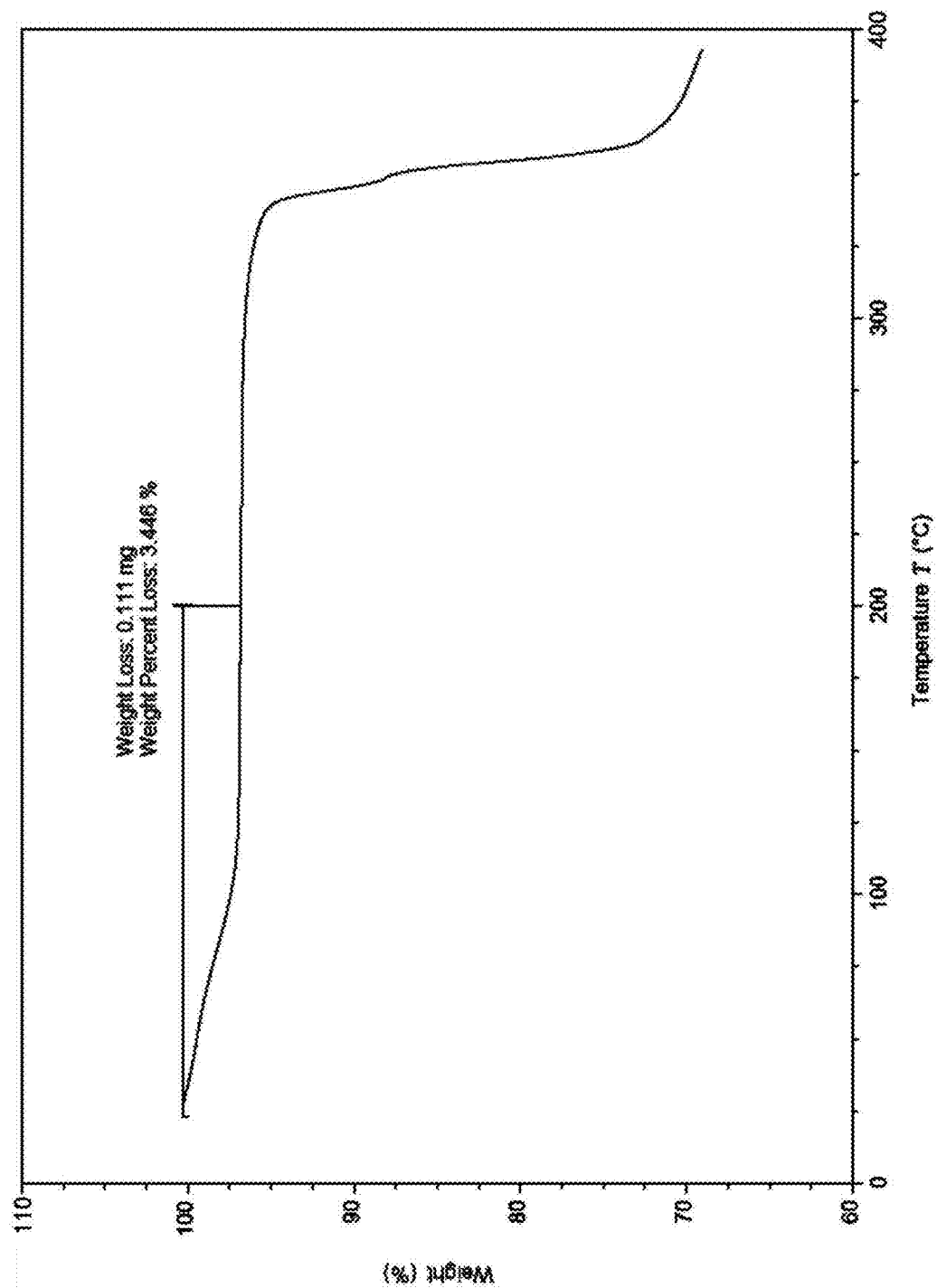
FIG. 22: the TGA pattern of the crystal form VI of Compound 1.

50 mg of the crystal form I of Compound 1 prepared in accordance with the method of Example 2 was weighed and placed in 1 mL of methanol, suspended and slurried at room temperature for 70 hrs, and then filtered to give the crystal form VI of Compound 1. The obtained crystal form VI has an XRPD pattern as shown in FIG. 20, a DSC pattern as shown in FIG. 21, and a TGA pattern as shown in FIG. 22.

Example 12. Preparation Method of Crystal Form VII of Compound 1

Figure 23:
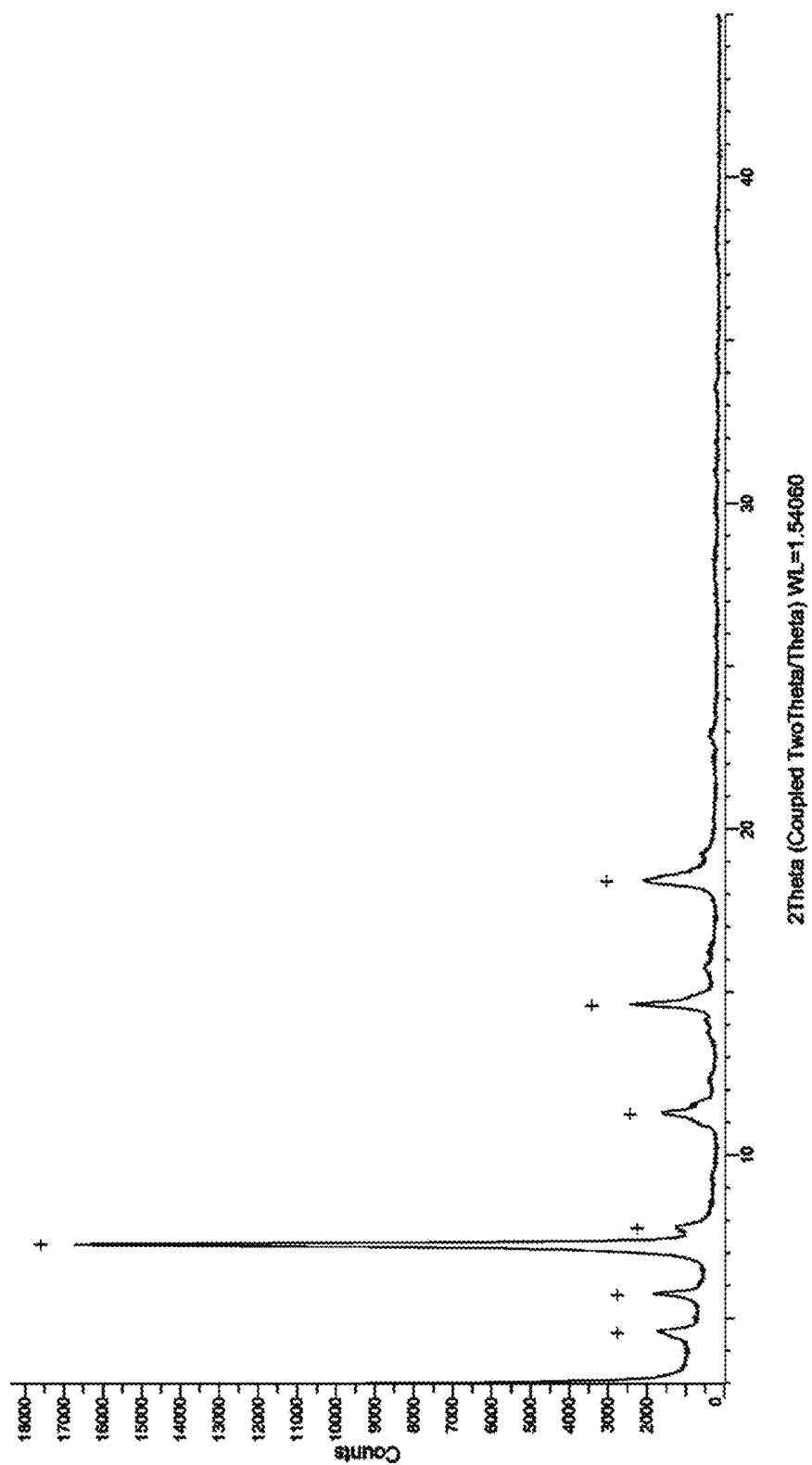
FIG. 23: the XRPD pattern of the crystal form VII of Compound 1.
Figure 24:
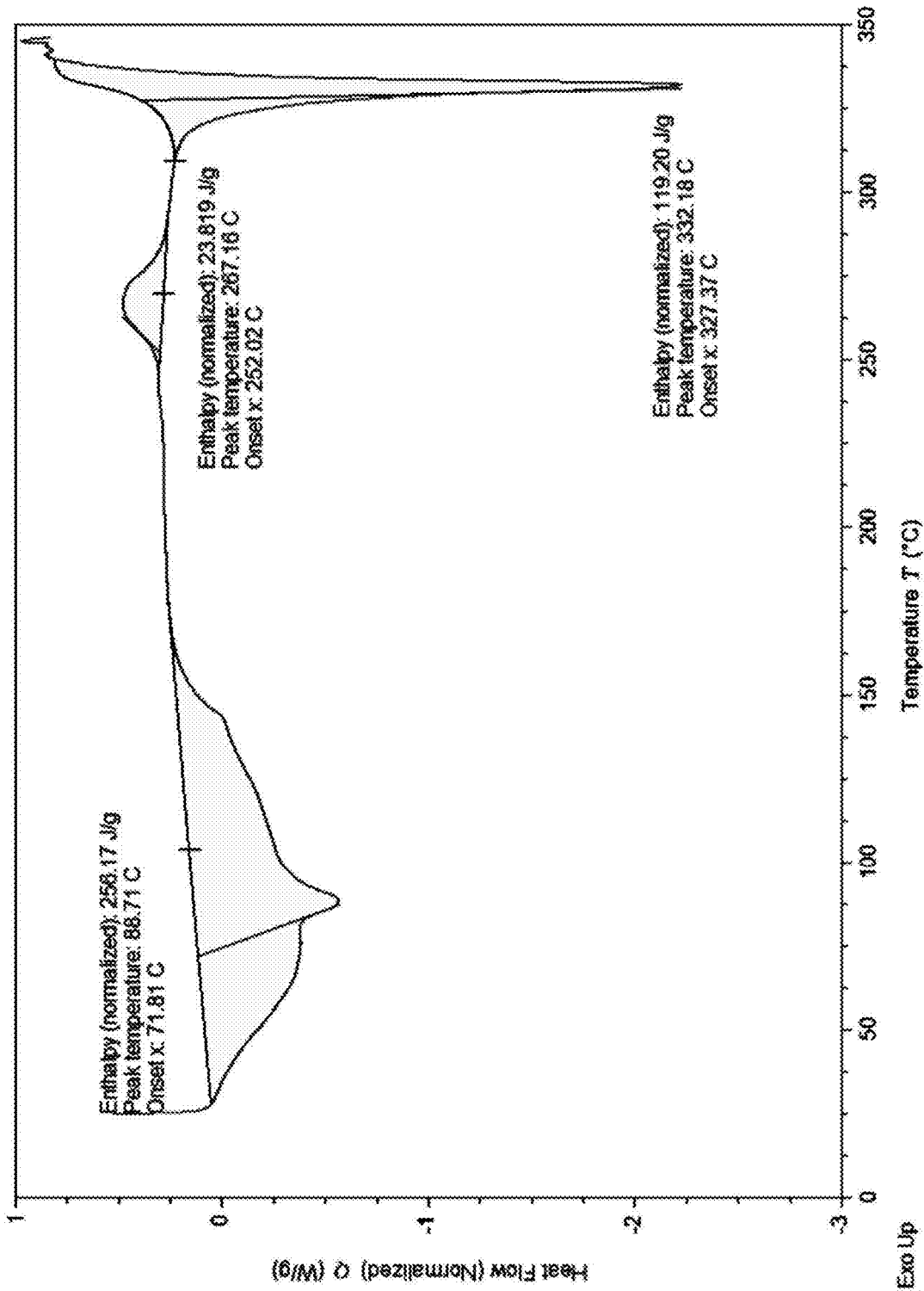
FIG. 24: the DSC pattern of the crystal form VII of Compound 1.
Figure 25:
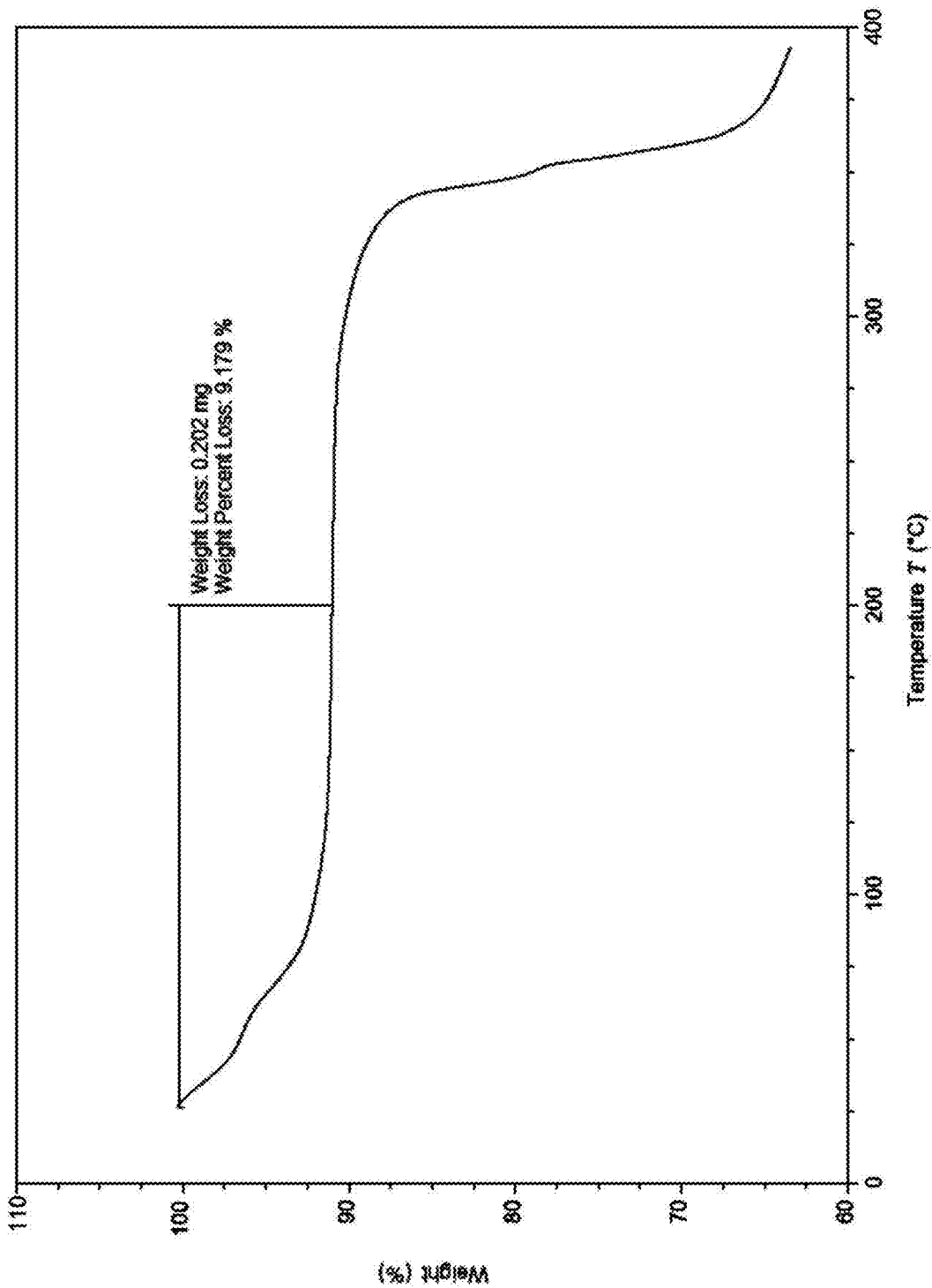
FIG. 25: the TGA pattern of the crystal form VII of Compound 1.

An appropriate amount of Compound 1 prepared in accordance with the method of Example 1 was weighed and dissolved in water to prepare a saturated solution. 200 μL of the saturated solution was added dropwise into 1.5 mL of acetonitrile at room temperature with stirring. After stirring at room temperature for 19 hrs, the mixture was centrifuged for solid-liquid separation. The obtained solid was detected, and the XRPD results indicated that the solid was a novel crystal form IX. The obtained solid was dried under vacuum at room temperature to give the crystal form VII of Compound 1. The obtained crystal form VII has an XRPD pattern as shown in FIG. 23, a DSC pattern as shown in FIG. 24, and a TGA pattern as shown in FIG. 25.

Example 13. Preparation Method of Crystal Form VII of Compound 1

10 mg of the crystal form I of Compound 1 prepared in accordance with the method of Example 2 was weighed and suspended in 1 mL of acetonitrile. 200 μL of water was added dropwise at 60° C. until the solid was completely dissolved. Then, the mixture was cooled to room temperature, stirred for 3 hrs, and centrifuged for solid-liquid separation. The obtained solid was detected. The XRPD of the solid indicated that it was a novel crystal form IX. The obtained solid was dried at room temperature under vacuum to give the crystal form VII of Compound 1.

Figure 26:
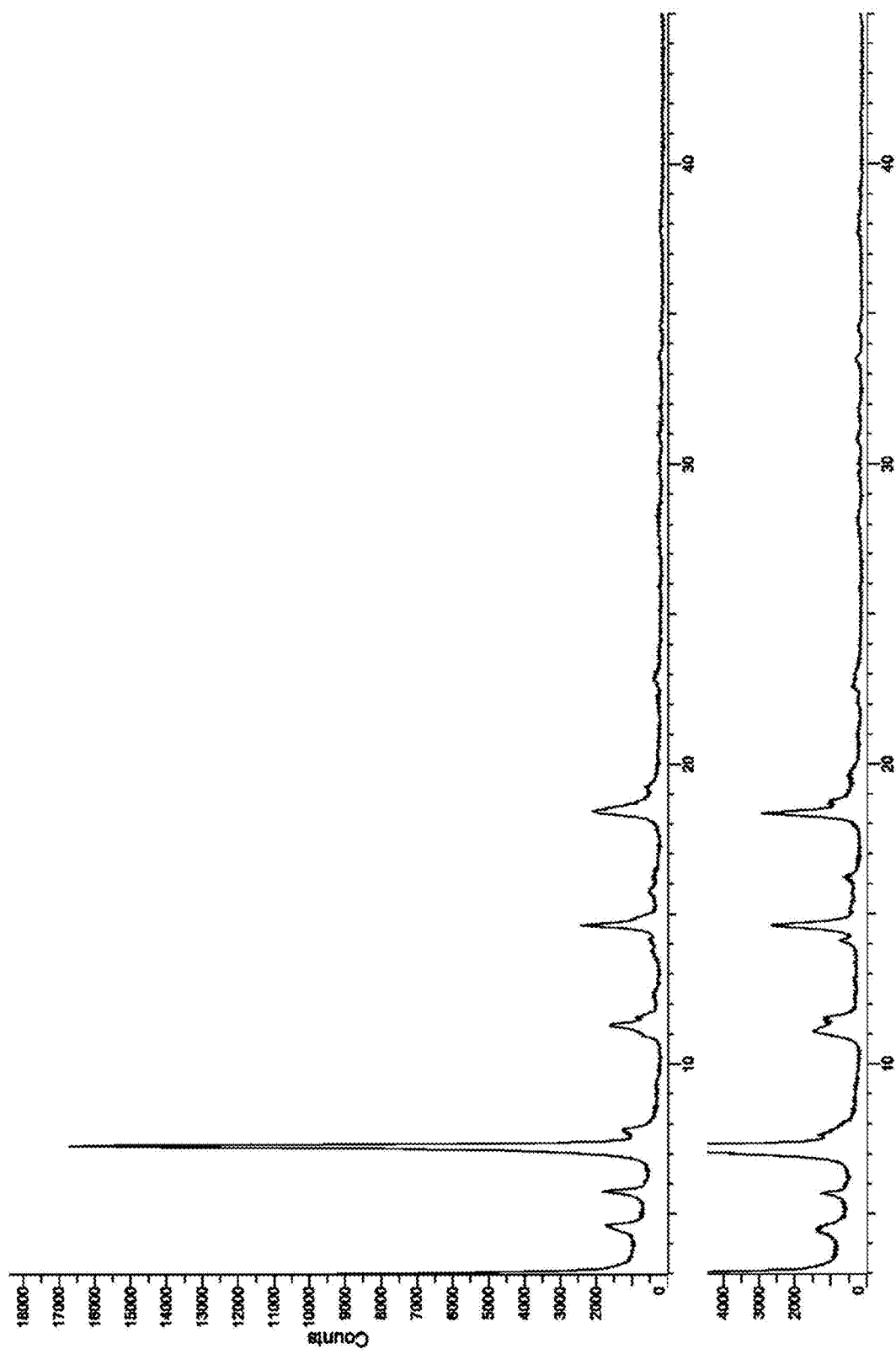
FIG. 26: the XRPD comparison pattern of the crystal form VII of Compound 1.

The XRPD comparison pattern of the crystal form VII is as shown in FIG. 26.

Example 14. Preparation Method of Crystal Form VIII of Compound 1

Figure 27:
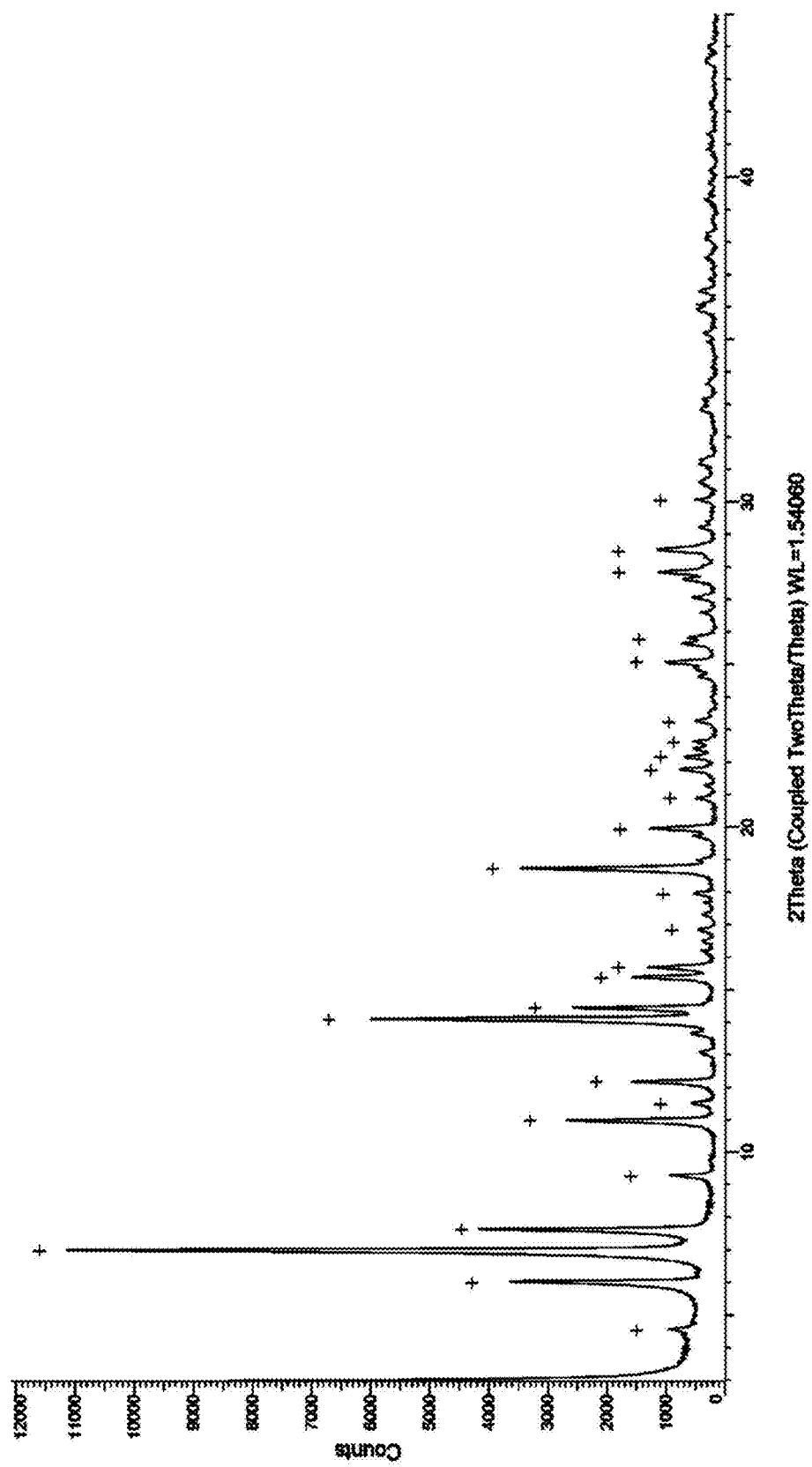
FIG. 27: the XRPD pattern of the crystal form VIII of Compound 1.
Figure 28:
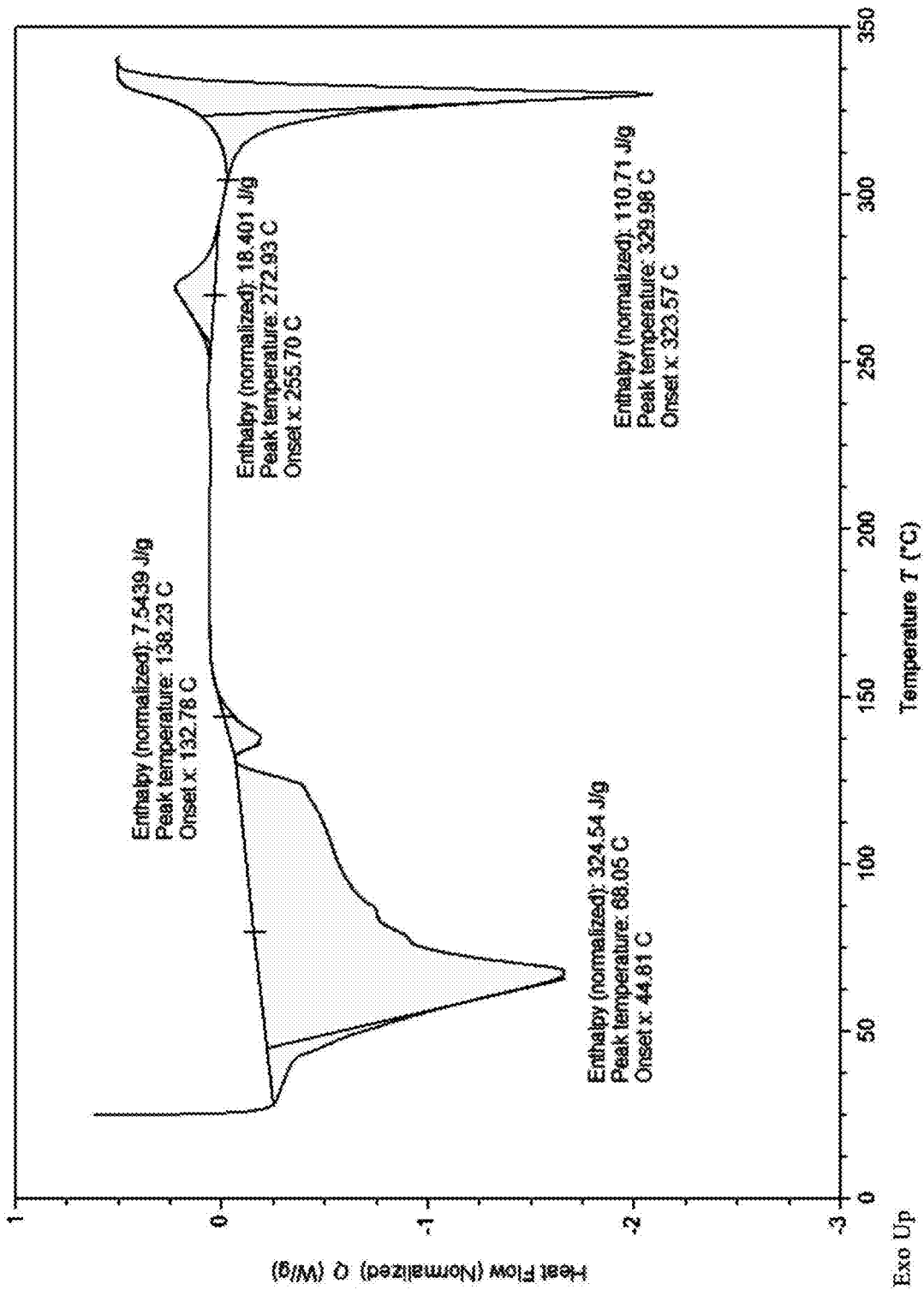
FIG. 28: the DSC pattern of the crystal form VIII of Compound 1.
Figure 29:
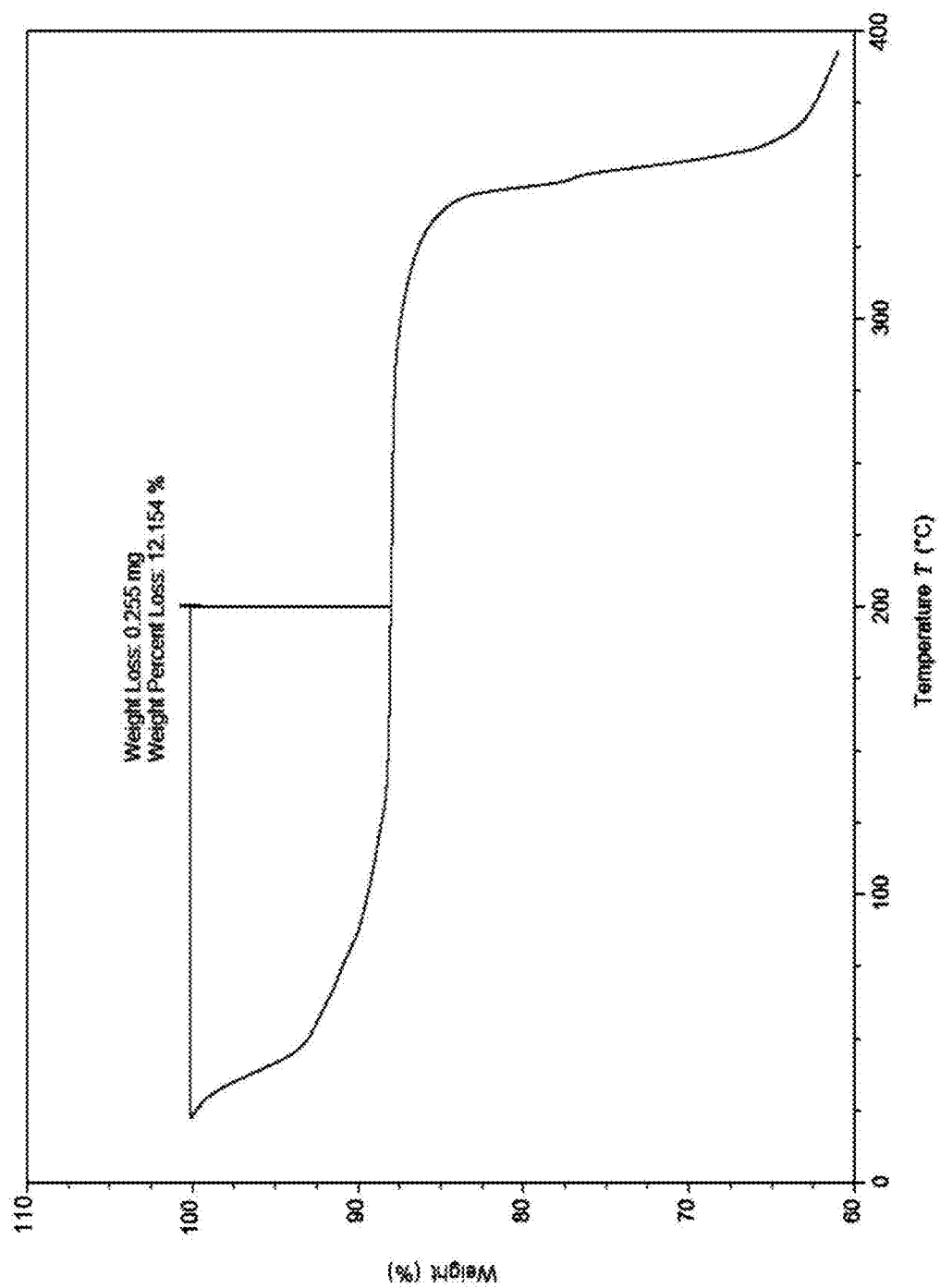
FIG. 29: the TGA pattern of the crystal form VIII of Compound 1.

An appropriate amount of Compound 1 prepared in accordance with the method of Example 1 was weighed and dissolved in water to prepare a saturated solution. 1 mL of the saturated solution was added dropwise into 1.5 mL of acetonitrile at room temperature with stirring. After stirring at room temperature for 19 hrs, the mixture was filtered at the atmosphere. The wet filter cake was detected, and the XRPD results indicated that the solid was a novel crystal form IX. The filter cake was air-dried at room temperature to give the crystal form VIII of Compound 1. The obtained crystal form VIII has an XRPD pattern as shown in FIG. 27, a DSC pattern as shown in FIG. 28, and a TGA pattern as shown in FIG. 29.

Figure 30:
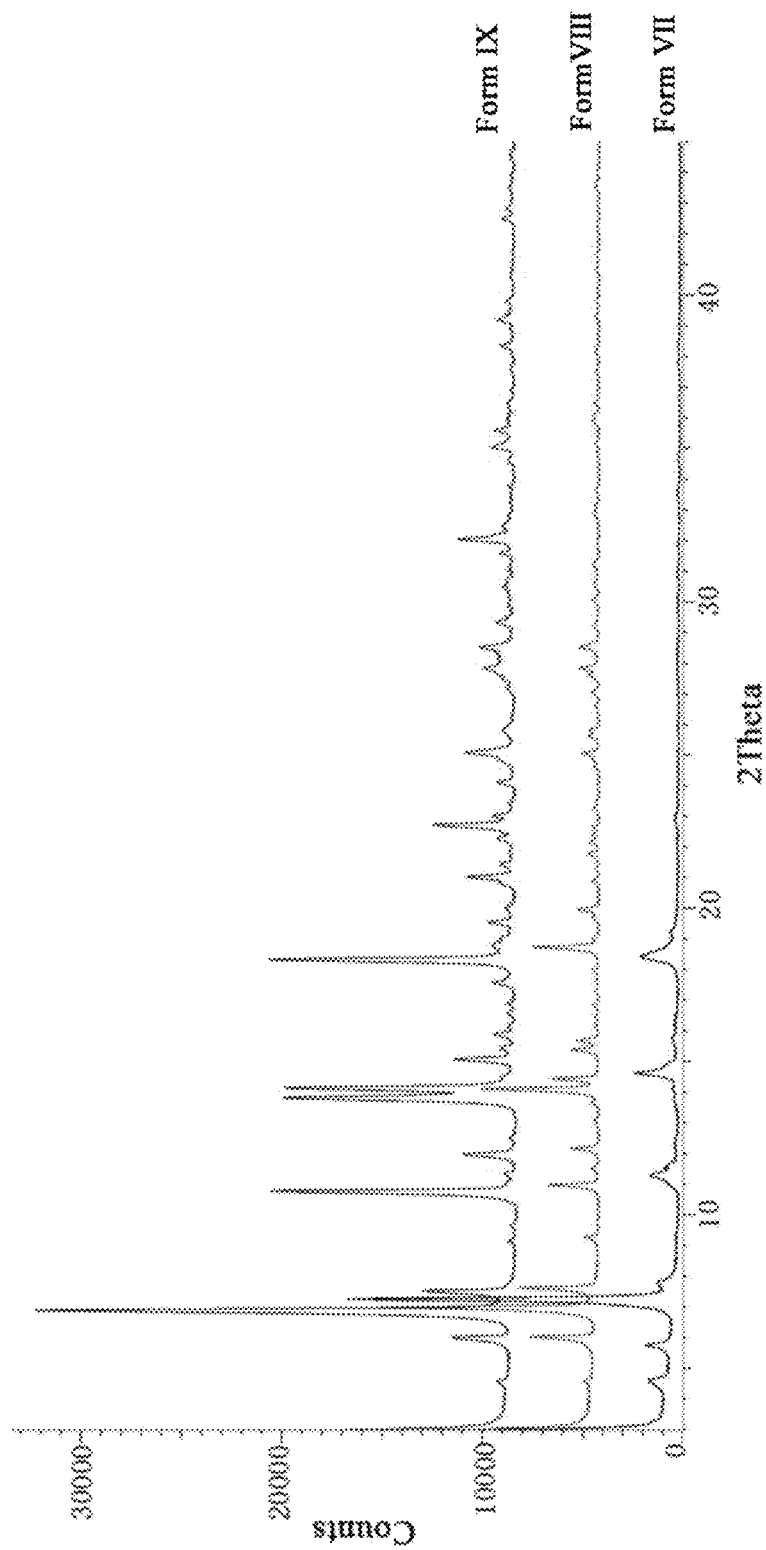
FIG. 30: the comparison of the XRPD patterns of the crystal form IX, the crystal form VII, and the crystal VIII of Compound 1.

The comparison of XRPD patterns of the obtained crystal form VII, crystal form VIII, and crystal form IX are as shown in FIG. 30.

Example 15. Solubility of Compound 1

Compound 1 was detected at room temperature for its solubility in 19 types of solvents. Specially, Compound 1 obtained in Example 1 was taken as sample for detecting its solubility in methanol, ethanol, water, acetonitrile, dioxane and other solvents. The results are shown in Table 1:

TABLE 1

| | Results of Solubility Tests | | |
|---|---|---|---|
| Solvent | Amount (µL) | Phenomenon | Solubility (mg/mL) |
| Methanol | 500 | Dissolved and clear | 20 < S < 50 |
| Ethanol | 3000 | Not dissolved completely at 50° C. | S < 3.3 |
| N-propanol | 3000 | Not dissolved completely at 50° C. | S < 3.3 |
| Iso-propanol | 3000 | Not dissolved completely at 50° C. | S < 3.3 |
| Acetone | 3000 | Not dissolved completely at 50° C. | S < 3.3 |
| Methyl isobutyl ketone | 3000 | Not dissolved completely at 50° C. | S < 3.3 |
| Ethyl acetate | 3000 | Not dissolved completely at 50° C. | S < 3.3 |
| Ethyl formate | 3000 | Not dissolved completely at 50° C. | S < 3.3 |
| Tetrahydrofuran | 3000 | Not dissolved completely at 50° C. | S < 3.3 |
| Acetonitrile | 3000 | Not dissolved completely at 50° C. | S < 3.3 |
| Dioxane | 3000 | Not dissolved completely at 50° C. | S < 3.3 |
| Dichloromethane | 3000 | Not dissolved completely at 50° C. | S < 3.3 |
| N-hexane | 3000 | Not dissolved completely at 50° C. | S < 3.3 |
| Methyl tert-butyl ether | 3000 | Not dissolved completely at 50° C. | S < 3.3 |
| Ethylene glycol monomethyl ether | 200 | Dissolved and clear | S > 50 |
| Ethylene glycol dimethyl ether | 3000 | Not dissolved completely at 50° C. | S < 3.3 |
| Dimethylformamide | 200 | Dissolved and clear | S > 50 |
| Dimethylsulfoxide | 200 | Dissolved and clear | S > 50 |
| Water | 200 | Dissolved and clear | S > 50 |

The above results show that the solubility of Compound 1 as a whole is better than that of WX-216. Specially, Compound 1 has good solubility in water, methanol, ethylene glycol monomethyl ether, dimethylformamide, dimethylsulfoxide, and relatively poor solubility in other solvents. Its advantages in solubility exceed a reasonable prediction of those skilled in the art.

Example 16. Study of Stability

An amount of sample to be tested was weighed and placed in a dish under conditions including high temperature (60° C.), high humidity (25° C., 92.5% RH), light radiation (25° C., 4500 Lux) and acceleration conditions (40° C., 75% RH), respectively, and sampled for XRPD characterization on day 14.

Form I, Form II, Form III were taken for stability study under conditions including high temperature (60° C.), high humidity (25° C., 92.5% RH), light radiation (25° C., 4500 Lux), and acceleration conditions (40° C., 75% RH), and the results are shown in Table 2:

TABLE 2

Results of Stability Study

| Crystal Form | Conditions | Results on Day 14 |
|---|---|---|
| Crystal Form I | High temperature | No changes |
| | High humidity | No changes |
| | Light radiation | No changes |
| | Acceleration conditions | No changes |
| Crystal Form II | High temperature | No changes |
| | High humidity | No changes |
| | Light radiation | No changes |
| | Acceleration conditions | No changes |
| Crystal Form III | High temperature | No changes |
| | High humidity | No changes |
| | Light radiation | No changes |
| | Acceleration conditions | No changes |

The results show that the crystal forms I-III have high stability under all the conditions of high temperature, high humidity, light radiation and acceleration conditions.

The crystal form I and the crystal form III can also be used as intermediate crystal forms for further producing some other stable crystal forms of the present disclosure.

Moreover, during the experiment and further study, the inventor further found out the follows:

The crystal form IV is obtained by heating the crystal form III to lose some crystalline water. The XRPD results show that the crystal form of crystal form IV does not change after DVS test, and it is considered that the crystal form IV has good stability.

The crystal form V can be obtained by long-term stirring in a methanol/iso-propyl acetate system at room temperature, followed by crystallization. Those skilled in the art can appreciate that the crystal form V has good stability.

The crystal form VI is an unstable crystal form, which is transformed to a crystal form V during post-treatment (drying under vacuum at ambient temperature). It can be seen that the crystal form V is finally obtained by the transition from an intermediate metastable crystal form (crystal form VI), and has high stability.

The crystal form VII and the crystal form VIII can be obtained by similar method but by different post-treatment means. During the experiment, an intermediate metastable crystal form (that is, the crystal form IX) is captured. It can be seen that the crystal form VII and the crystal form VIII are both obtained by the transition of the intermediate metastable crystal form (i.e., the crystal form IX) and have high stability.

In sum, the crystal forms of Compound 1 of the present disclosure have at least one of the effects of stability and solubility, and provide a variety of options of intermediate products and/or APIs for large-scale production of APIs and downstream processes of pharmaceutical products (e.g., the preparation process).

The above examples are preferable embodiments of the present disclosure. However, the embodiments of the present disclosure are not limited to the above examples, and any other variations, modifications, substitutions, combinations and simplifications without departing from the spirits and principles of the present disclosure are equivalent replacement embodiments and encompassed within the protection scope of the present disclosure.

The invention claimed is:

1. A crystal form of Compound 1, comprising a crystal form I, a crystal form II, a crystal form III, a crystal form IV, a crystal form V, a crystal form VII or a crystal form VIII,

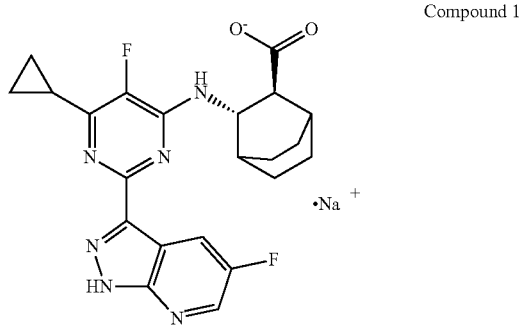

Compound 1 wherein,
(i) an XRPD pattern of the crystal form I of Compound 1 has diffraction peaks at angles 2θ of 6.4, 9.8, 12.8, 15.8, 16.2, 17.8, 18.7, 19.3, 20.3, 24.0, 24.6, 27.6, 28.1±0.2°;
(ii) an XRPD pattern of the crystal form II of Compound 1 has diffraction peaks at angles 2θ of 5.8, 9.3, 10.0, 11.6, 13.7, 17.0, 18.9, 22.8, 24.2±0.2°;
(iii) an XRPD pattern of the crystal form III of Compound 1 has diffraction peaks at angles 2θ of 4.6, 5.4, 7.1, 9.7, 10.8, 12.4, 15.1, 17.0, 17.8, 18.9, 19.6, 20.7, 21.8, 23.7, 25.0±0.2°;
(iv) an XRPD pattern of the crystal form IV of Compound 1 has diffraction peaks at angles 2θ of 5.7, 6.9, 9.3, 12.3, 14.3, 16.7, 17.8, 18.7, 19.3, 20.6, 23.8, 28.4±0.2°;
(v) an XRPD pattern of the crystal form V of Compound 1 has diffraction peaks at angles 2θ of 7.1, 9.4, 12.3, 15.5, 18.8, 19.8, 20.9, 25.5, 27.1±0.2°;

(vi) an XRPD pattern of the crystal form VII of Compound 1 has diffraction peaks at angles 2θ of 4.6, 5.8, 7.3, 7.8, 11.3, 14.6, 18.4±0.2°; and (vii) an XRPD pattern of the crystal form VIII of Compound 1 has diffraction peaks at angles 2θ of 6.0, 7.0, 7.6, 11.0, 12.2, 14.1, 14.4, 15.4, 18.7, 20.0, 27.8±0.2°.

2. The crystal form of Compound 1 according to claim 1, wherein (i) the XRPD pattern of the crystal form I of Compound 1 further has diffraction peaks at angles 2θ of 9.0, 15.3, 17.4, 23.1, 28.4±0.2°;

(ii) the XRPD pattern of the crystal form II of Compound 1 further has diffraction peaks at angles 2θ of 12.4, 17.7, 21.0, 22.2, 30.1±0.2°;

(iii) the XRPD pattern of the crystal form III of Compound 1 further has diffraction peaks at angles 2θ of 13.6, 14.1, 20.1, 21.3, 24.3, 26.1, 26.5, 28.4, 30.0±0.2°;

(iv) the XRPD pattern of the crystal form IV of Compound 1 further has diffraction peaks at angles 2θ of 18.2, 18.9, 19.5, 21.6, 27.2, 30.5±0.2°;

(v) the XRPD pattern of the crystal form V of Compound 1 further has diffraction peaks at angles 2θ of 12.8, 16.0, 16.3, 16.5, 20.0, 21.4, 22.2, 22.5, 23.3, 24.7, 25.7, 26.5, 31.2±0.2°; and (vi) the XRPD pattern of the crystal form VIII of Compound 1 further has diffraction peaks at angles 2θ of 4.6, 9.3, 15.7, 21.8, 22.2, 25.0, 28.5±0.2°.

3. The crystal form of Compound 1 according to claim 1, wherein (i) the diffraction peaks of the XRPD pattern of the crystal form I of Compound 1 are as shown in the table below:

| No. | 2θ (±0.2°) |
|---|---|
| 1 | 6.4 |
| 2 | 9.0 |
| 3 | 9.8 |
| 4 | 12.8 |
| 5 | 14.4 |
| 6 | 15.3 |
| 7 | 15.8 |
| 8 | 16.2 |
| 9 | 17.4 |
| 10 | 17.8 |
| 11 | 18.7 |
| 12 | 19.3 |
| 13 | 20.3 |
| 14 | 21.4 |
| 15 | 22.1 |
| 16 | 23.1 |
| 17 | 23.6 |
| 18 | 24.0 |
| 19 | 24.2 |
| 20 | 24.6 |
| 21 | 26.3 |
| 22 | 26.5 |
| 23 | 27.6 |
| 24 | 28.1 |
| 25 | 28.4 |
| 26 | 28.8 |
| 27 | 29.8 |
| 28 | 35.2 |

(ii) the diffraction peaks of the XRPD pattern of the crystal form II of Compound 1 are as shown in the table below:

| No. | 2θ (±0.2°) |
|---|---|
| 1 | 5.8 |
| 2 | 9.3 |
| 3 | 10.0 |
| 4 | 11.6 |
| 5 | 12.4 |
| 6 | 13.7 |
| 7 | 15.3 |
| 8 | 17.0 |
| 9 | 17.7 |
| 10 | 18.9 |
| 11 | 21.0 |
| 12 | 21.2 |
| 13 | 22.2 |
| 14 | 22.8 |
| 15 | 24.2 |
| 16 | 24.9 |
| 17 | 25.4 |
| 18 | 26.5 |
| 19 | 30.1 |

(iii) the diffraction peaks of the XRPD pattern of the crystal form III of Compound 1 are as shown in the table below:

| No. | 2θ (±0.2°) |
|---|---|
| 1 | 4.6 |
| 2 | 5.4 |
| 3 | 7.1 |
| 4 | 9.7 |
| 5 | 10.8 |
| 6 | 12.4 |
| 7 | 13.6 |
| 8 | 14.1 |
| 9 | 15.1 |
| 10 | 16.3 |
| 11 | 17.0 |
| 12 | 17.8 |
| 13 | 18.9 |
| 14 | 19.6 |
| 15 | 20.1 |
| 16 | 20.7 |
| 17 | 21.3 |
| 18 | 21.8 |
| 19 | 22.3 |
| 20 | 23.7 |
| 21 | 24.3 |
| 22 | 25.0 |
| 23 | 25.6 |
| 24 | 26.1 |
| 25 | 26.5 |
| 26 | 27.4 |
| 27 | 28.2 |
| 28 | 28.4 |
| 29 | 30.0 |

(iv) the diffraction peaks of the XRPD pattern of the crystal form IV of Compound 1 are as shown in the table below:

| No. | 2θ (±0.2°) |
|---|---|
| 1 | 5.7 |
| 2 | 6.9 |
| 3 | 9.3 |

-continued

| No. | 2θ (±0.2°) |
|---|---|
| 4 | 9.9 |
| 5 | 12.3 |
| 6 | 13.9 |
| 7 | 14.3 |
| 8 | 15.5 |
| 9 | 16.2 |
| 10 | 16.7 |
| 11 | 17.8 |
| 12 | 18.2 |
| 13 | 18.7 |
| 14 | 18.9 |
| 15 | 19.3 |
| 16 | 19.5 |
| 17 | 20.6 |
| 18 | 20.9 |
| 19 | 21.6 |
| 20 | 22.4 |
| 21 | 23.5 |
| 22 | 23.8 |
| 23 | 24.2 |
| 24 | 25.0 |
| 25 | 25.9 |
| 26 | 27.2 |
| 27 | 27.7 |
| 28 | 28.4 |
| 29 | 29.4 |
| 30 | 30.5 |

(v) the diffraction peaks of the XRPD pattern of the crystal form V of Compound 1 are as shown in the table below:

| No. | 2θ (±0.2°) |
|---|---|
| 1 | 7.1 |
| 2 | 9.4 |
| 3 | 12.3 |
| 4 | 12.8 |
| 5 | 14.2 |
| 6 | 15.5 |
| 7 | 16.0 |
| 8 | 16.3 |
| 9 | 16.5 |
| 10 | 16.8 |
| 11 | 17.9 |
| 12 | 18.8 |
| 13 | 19.8 |
| 14 | 20.0 |
| 15 | 20.9 |
| 16 | 21.4 |
| 17 | 22.2 |
| 18 | 22.5 |
| 19 | 23.3 |
| 20 | 24.7 |
| 21 | 25.0 |
| 22 | 25.5 |
| 23 | 25.7 |
| 24 | 26.5 |
| 25 | 27.1 |
| 26 | 28.3 |
| 27 | 30.5 |
| 28 | 31.2 |
| 29 | 32.9 |

(vi) the diffraction peaks of the XRPD pattern of the crystal form VII of Compound 1 are as shown in the table below:

| No. | 2θ (±0.2°) |
|---|---|
| 1 | 4.6 |
| 2 | 5.8 |
| 3 | 7.3 |
| 4 | 7.8 |
| 5 | 11.3 |
| 6 | 14.6 |
| 7 | 18.4 | and (vii) the diffraction peaks of the XRPD pattern of the crystal form VIII of Compound 1 are as shown in the table below:

| No. | 2θ (±0.2°) |
|---|---|
| 1 | 4.6 |
| 2 | 6.0 |
| 3 | 7.0 |
| 4 | 7.6 |
| 5 | 9.3 |
| 6 | 11.0 |
| 7 | 11.5 |
| 8 | 12.2 |
| 9 | 14.1 |
| 10 | 14.4 |
| 11 | 15.4 |
| 12 | 15.7 |
| 13 | 16.9 |
| 14 | 18.0 |
| 15 | 18.7 |
| 16 | 20.0 |
| 17 | 20.9 |
| 18 | 21.8 |
| 19 | 22.2 |
| 20 | 22.6 |
| 21 | 23.3 |
| 22 | 25.0 |
| 23 | 25.7 |
| 24 | 27.8 |
| 25 | 28.5 |
| 26 | 30.1 |

4. The crystal form of Compound 1 according to claim 1, wherein
   (i) the XRPD pattern of the crystal form I of Compound 1 is substantially as shown in FIG. 1;
   (ii) the XRPD pattern of the crystal form II of Compound 1 is substantially as shown in FIG. 5;
   (iii) the XRPD pattern of the crystal form III of Compound 1 is substantially as shown in FIG. 9;
   (iv) the XRPD pattern of the crystal form IV of Compound 1 is substantially as shown in FIG. 13;
   (v) the XRPD pattern of the crystal form V of Compound 1 is substantially as shown in FIG. 16;
   (vi) the XRPD pattern of the crystal form VII of Compound 1 is substantially as shown in FIG. 23; and
   (vii) the XRPD pattern of the crystal form VIII of Compound 1 is substantially as shown in FIG. 27.

5. The crystal form of Compound 1 according to claim 1, wherein
   (i) a DSC pattern of the crystal form I of Compound 1 has starting points of endothermic peaks at 51.6, 158.2, and 335.9±3° C., and a starting point of an exothermic peak at 230.4±3° C.;
   (ii) a DSC pattern of the crystal form II of Compound 1 has a starting point of an endothermic peak at 335.9=3° C.;

(iii) a DSC pattern of the crystal form III of Compound 1 has starting points of endothermic peaks at 33.5, and 329.0±3° C., and a starting point of an exothermic peak at 272.1±3° C.;
(iv) a DSC pattern of the crystal form IV of Compound 1 has a starting point of an endothermic peak at 326.3±3° C.;
(v) a DSC pattern of the crystal form V of Compound 1 has a starting point of an endothermic peak at 339.1±3° C.;
(vi) a DSC pattern of the crystal form VII of Compound 1 has starting points of endothermic peaks at 71.8±3° C., and 327.4±3° C., and a starting point of an exothermic peak at 252.0±3° C.; and
(vii) a DSC pattern of the crystal form VIII of Compound 1 has starting points of endothermic peaks at 44.8±3° C., 132.8±3° C., and 323.6±3° C., and a starting point of an exothermic peak at 255.7±3° C.

6. The crystal form of Compound 1 according to claim 1, wherein
(i) the DSC pattern of the crystal form I of Compound 1 is substantially as shown in FIG. 2;
(ii) the DSC pattern of the crystal form II of Compound 1 is substantially as shown in FIG. 6;
(iii) the DSC pattern of the crystal form III of Compound 1 is substantially as shown in FIG. 10;
(iv) the DSC pattern of the crystal form IV of Compound 1 is substantially as shown in FIG. 14;
(v) the DSC pattern of the crystal form V of Compound 1 is substantially as shown in FIG. 17;
(vi) the DSC pattern of the crystal form VII of Compound 1 is substantially as shown in FIG. 24; and
(vii) the DSC pattern of the crystal form VIII of Compound 1 is substantially as shown in FIG. 28.

7. The crystal form of Compound 1 according to claim 1, wherein
(i) a TGA pattern of the crystal form I of Compound 1 exhibits a weight loss of 12.06=1% at 200° C.;
(ii) a TGA pattern of the crystal form II of Compound 1 does not exhibit a remarkable weight loss before 300° C.;
(iii) a TGA pattern of the crystal form III of Compound 1 exhibits a weight loss of 11.40±1% at 200° C.;
(iv) a TGA pattern of the crystal form IV of Compound 1 does not exhibit a remarkable weight loss before 300° C.;
(v) a TGA pattern of the crystal form V of Compound 1 exhibits a weight loss of 1.26±1% before 75° C.;
(vi) a TGA pattern of the crystal form VII of Compound 1 exhibits a weight loss of 9.18=1% at 200° C.; and
(vii) a TGA pattern of the crystal form VIII of Compound 1 exhibits a weight loss of 12.15±1% at 200° C.

8. The crystal form of Compound 1 according to claim 7, the crystal form I of Compound 1 exhibits a weight loss of 5.85±1% at 100° C., followed by an additional weight loss of 6.21±1% at 200° C.

9. The crystal form of Compound 1 according to claim 7, wherein
(i) the TGA pattern of the crystal form I of Compound 1 is substantially as shown in FIG. 3;

(ii) the TGA pattern of the crystal form II of Compound 1 is substantially as shown in FIG. 7;
(iii) the TGA pattern of the crystal form III of Compound 1 is substantially as shown in FIG. 11;
(iv) the TGA pattern of the crystal form IV of Compound 1 is substantially as shown in FIG. 15;
(v) the TGA pattern of the crystal form V of Compound 1 is substantially as shown in FIG. 18;
(vi) the TGA pattern of the crystal form VII of Compound 1 is substantially as shown in FIG. 25; and
(vii) the TGA pattern of the crystal form VIII of Compound 1 is substantially as shown in FIG. 29.

10. An active pharmaceutical ingredient comprising Compound 1 and/or WX-216 and/or other salt forms of WX-216, wherein the active pharmaceutical ingredient comprises at least one crystal form of Compound 1 according to claim 1.

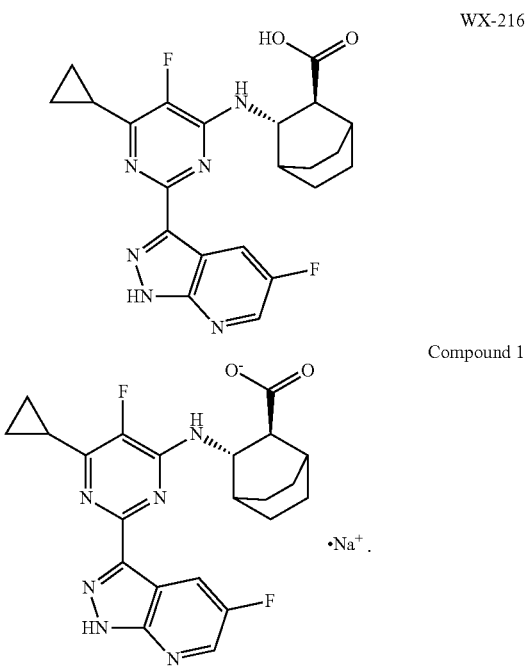

11. An active pharmaceutical ingredient comprising Compound 1 and/or WX-216 and/or other salt forms of WX-216, wherein the active pharmaceutical ingredient comprises at least one crystal form of Compound 1 according to claim 5.

12. An active pharmaceutical ingredient comprising Compound 1 and/or WX-216 and/or other salt forms of WX-216, wherein the active pharmaceutical ingredient comprises at least one crystal form of Compound 1 according to claim 7.

13. A pharmaceutical composition consisting of the active pharmaceutical ingredient of claim 10 and a pharmaceutically acceptable excipient.

14. The pharmaceutical composition according to claim 13, wherein the pharmaceutically acceptable excipient is at least one selected from the group consisting of fillers, binders, disintegrants, and lubricants.

* * * * *